(12) United States Patent
Wild

(10) Patent No.: US 9,751,930 B2
(45) Date of Patent: Sep. 5, 2017

(54) PROCESS FOR PURIFYING PROTEINS

(75) Inventor: Gavin Barry Wild, Slough (GB)

(73) Assignee: UCB PHARMA, S.A., Brussels (BE)

( * ) Notice: Subject to any disclaimer, the term of this patent is extended or adjusted under 35 U.S.C. 154(b) by 0 days.

(21) Appl. No.: 13/812,350

(22) PCT Filed: Jul. 27, 2011

(86) PCT No.: PCT/GB2011/001129
§ 371 (c)(1),
(2), (4) Date: Mar. 25, 2013

(87) PCT Pub. No.: WO2012/013930
PCT Pub. Date: Feb. 2, 2012

(65) Prior Publication Data
US 2013/0178607 A1    Jul. 11, 2013

(30) Foreign Application Priority Data
Jul. 27, 2010   (GB) .................................. 1012599.5

(51) Int. Cl.
| C07K 16/00 | (2006.01) |
| C07K 1/30 | (2006.01) |
| C12N 9/90 | (2006.01) |
| C12P 21/00 | (2006.01) |
| C07K 16/24 | (2006.01) |

(52) U.S. Cl.
CPC ................ *C07K 16/00* (2013.01); *C07K 1/30* (2013.01); *C07K 16/241* (2013.01); *C12N 9/90* (2013.01); *C12P 21/00* (2013.01); *C07K 2317/14* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 5,264,365 A | 11/1993 | Georgiou et al. | |
| 5,508,192 A | 4/1996 | Georgiou et al. | |
| 5,665,866 A | 9/1997 | Weir et al. | |
| 6,027,888 A * | 2/2000 | Georgiou | C07K 14/8117 435/243 |
| 6,083,715 A * | 7/2000 | Georgiou et al. | 435/69.1 |
| 6,306,619 B1 | 10/2001 | Jones et al. | |
| 7,012,135 B2 * | 3/2006 | Athwal et al. | 530/388.23 |
| 7,041,479 B2 * | 5/2006 | Swartz et al. | 435/70.1 |
| 7,419,659 B2 | 9/2008 | Popplewell | |
| 7,662,587 B1 | 2/2010 | Cheng et al. | |
| 8,293,237 B2 | 10/2012 | Burkly et al. | |
| 8,470,552 B2 | 6/2013 | Croughan et al. | |
| 8,784,823 B2 | 7/2014 | Burkly et al. | |
| 8,969,037 B2 | 3/2015 | Ellis et al. | |
| 8,969,038 B2 | 3/2015 | Ellis et al. | |
| 8,969,039 B2 | 3/2015 | Ellis et al. | |
| 9,109,216 B2 | 8/2015 | Ellis et al. | |
| 9,493,558 B2 | 11/2016 | Ellis et al. | |
| 9,493,559 B2 | 11/2016 | Ellis et al. | |
| 9,550,973 B2 | 1/2017 | Ellis et al. | |
| 2005/0048572 A1 * | 3/2005 | Reilly | C07K 16/22 435/7.1 |
| 2006/0204493 A1 | 9/2006 | Huang et al. | |
| 2009/0252743 A1 | 10/2009 | Heavner et al. | |
| 2010/0104573 A1 | 4/2010 | Burkly et al. | |
| 2011/0111408 A1 | 5/2011 | Marrichi et al. | |
| 2012/0258492 A1 | 10/2012 | Ellis et al. | |
| 2012/0288894 A1 | 11/2012 | Ellis et al. | |
| 2012/0295309 A1 | 11/2012 | Ellis et al. | |
| 2012/0301920 A1 | 11/2012 | Ellis et al. | |
| 2013/0045219 A1 | 2/2013 | Burkly et al. | |
| 2013/0060009 A1 | 3/2013 | Bilgischer et al. | |
| 2014/0141468 A1 | 5/2014 | Ellis et al. | |
| 2014/0302016 A1 | 10/2014 | Burkly et al. | |
| 2015/0111249 A1 | 4/2015 | Bassett et al. | |
| 2015/0132828 A1 | 5/2015 | Ellis et al. | |
| 2015/0166651 A1 | 6/2015 | Ellis et al. | |

(Continued)

FOREIGN PATENT DOCUMENTS

| CN | 1549821 A | 11/2004 |
| EA | 007905 | 2/2007 |
| EP | 2 546 267 | 1/2013 |

(Continued)

OTHER PUBLICATIONS

Hu et al. 2007 (Optimisation of production of a domoic acid-binding scFv antibody fragment in *Escherichia coli* using molecular chaperones and functional immobilization on a mesoporous silicate support; Protein Expression and Purification 52: 194-201).*

Wunderlich et al. 1993 (Bacterial protein disulfide isomerase: efficient catalysis of oxidative protein folding at acidic pH; Biochemistry; 32(45):12251-6).*

Gehring et al. 2010 (Functional and nutritional quality of protein and lipid recovered from fish processing by-products and underutilized aquatic species using isoelectric solubilization/precipitation; Current Nutrition & Food Science, 5(1):17-39).*

Liu, Z. et al., "The Influence of Coexpression of TrxA and DsbC to the Expression of Heterogenous Protein with Multiple Disulfide Bonds" *Chinese Journal of Biochemistry and Molecular Biology*, Aug. 30, 2002, pp. 486-489, vol. 18, No. 4.

Want, a. et al. "Studies Related to Antibody Fragment (Fab) Production in *Escherichia coli* W3110 Fed-Batch Fermentation Processes Using Multiparameter Flow Cytometry" *Cytometry Part A*, Feb. 2009, pp. 148-154, vol. 75, No. 2.

(Continued)

*Primary Examiner* — Gary Nickol
*Assistant Examiner* — Mary Lyons
(74) *Attorney, Agent, or Firm* — Saliwanchik, Lloyd & Eisenschenk

(57) ABSTRACT

The present invention provides method for purifying a recombinant protein from a gram-negative bacterial host cell sample or extract thereof wherein said host cell expresses a recombinant protein and a recombinant disulphide isomerase DsbC; comprising: a. adjusting the pH of the host cell sample or extract thereof to a pH of 5 or less to precipitate the recombinant disulphide isomerase; and b. separating precipitated recombinant disulphide isomerase DsbC from the recombinant protein to produce a recombinant protein sample.

41 Claims, 21 Drawing Sheets

(56) References Cited

U.S. PATENT DOCUMENTS

| | | |
|---|---|---|
| 2015/0166652 A1 | 6/2015 | Ellis et al. |
| 2015/0344840 A1 | 12/2015 | Ellis et al. |

FOREIGN PATENT DOCUMENTS

| | | |
|---|---|---|
| WO | WO 98/56930 | 12/1998 |
| WO | WO 01/68860 | 9/2001 |
| WO | WO 02/18445 | 3/2002 |
| WO | WO 02/18446 | 3/2002 |
| WO | WO 02/48376 | 6/2002 |
| WO | WO 02/061090 | 8/2002 |
| WO | WO 03/018771 | 3/2003 |
| WO | WO 03/031475 | 4/2003 |
| WO | WO 03/048208 | 6/2003 |
| WO | WO 03/048306 | 6/2003 |
| WO | WO 2004/003019 | 1/2004 |
| WO | WO 2004/051268 | 6/2004 |
| WO | WO 2004/072116 | 8/2004 |
| WO | WO 2005/003175 | 1/2005 |
| WO | WO 2005/011376 | 2/2005 |
| WO | WO 2005/035572 | 4/2005 |
| WO | WO 2006/030220 | 3/2006 |
| WO | WO 2006/033702 | 3/2006 |
| WO | WO 2006/054063 | 5/2006 |
| WO | WO 2008/118356 | 10/2008 |
| WO | WO 2011/036454 | 3/2011 |
| WO | WO 2011/057120 | 5/2011 |
| WO | WO 2011/086136 | 7/2011 |
| WO | WO 2011/086138 A1 | 7/2011 |
| WO | WO 2011/086139 A1 | 7/2011 |
| WO | WO 2011/086141 A1 | 7/2011 |
| WO | WO 2011/095506 | 8/2011 |
| WO | WO 2013/007388 | 1/2013 |
| WO | WO 2013/171156 | 11/2013 |

OTHER PUBLICATIONS

Ponniah, K., et al., "The production of soluble and correctly folded recombinant bovine β-lactoglobulin variants A and B in Escherichia coli for NMR studies," Protein Expression and Purification, 2010, vol. 70, No. 2, pp. 283-289.

Pan, K.-L. et al. "Roles of DegP in Prevention of Protein Misfolding in the Periplasm upon Overexpression of Penicillin Acylase in Escherichia coli" Journal of Bacteriology, May 2003, pp. 3020-3030, vol. 185, No. 10.

Silber, K. R. et al. "Deletion of the prc (tsp) gene provides evidence for additional tail-specific proteolytic activity in Escherichia coli K-12" Mol. Gen Genet, 1994, vol. 242, pp. 237-240.

Chen, C. et al. "High-Level Accumulation of a Recombinant Antibody Fragment in the Periplasm of Escherichia coli Requires a Triple-Mutant (degP prc spr) Host Strain" Biotechnology and Bioengineering, Mar. 5, 2004, pp. 463-474, vol. 85, No. 5.

Database UniProt [Online] EBI Accession No. UNIPROT:B7UFJ2, Subname: Full=Predicted peptidase, outer membrane lipoprotein, Feb. 10, 2009, XP-002630316, p. 1.

Database UniProt [Online] EBI Accession No. UNIPROT:B7LAJ9, Subname: Full=Putative peptidase, outer membrane lipoprotein, Feb. 10, 2009, XP-002630317, p. 1.

Database UniProt [Online] EBI Accession No. UNIPROT:B7LJR7, Subname: Full=Putative peptidase, outer membrane lipoprotein, Feb. 10, 2009, XP-002630318, p. 1.

Database UniProt [Online] EBI Accession No. UNIPROT:C1M6L5, Subname: Full=Putative uncharacterized protein, May 26, 2009, XP-002630319, p. 1.

Hara, H. et al. "Overproduction of Penicillin-Binding Protein 7 Suppresses Thermosensitive Growth Defect at Low Osmolarity due to an spr Mutation of Escherichia coli" Microbial Drug Resistance, Jan. 1, 1996, pp. 63-72, vol. 2, No. 1.

Aramini, J. et al. "Solution NMR Structure of the NlpC/P60 Domain of Lipoprotein Spr from Escherichia coli: Structural Evidence for a Novel Cysteine Peptidase Catalytic Triad" Biochemistry, 2008, pp. 9715-9717, vol. 47.

Tadokoro, A. et al. "Interaction of the Escherichia coli Lipoprotein Nlpl with Periplasmic Prc (Tsp) Protease" Journal of Biochemistry, 2004, pp. 185-191, vol. 135.

Written Opinion in International Application No. PCT/EP2011/050415, Jun. 20, 2011, pp. 1-15.

O'Dwyer, R. et al. "Microarray-based analysis of recombinant protein production in E. coli" Microbial Cell Factories, 2006, pp. 1-2 vol. 5, Supp 1.

Maskos, K. et al. "DsbA and DsbC-catalyzed Oxidative Folding of Proteins with Complex Disulfide Bridge Patterns In Vitro and In Vivo" Journal of Molecular Biology, 2003, pp. 495-513, vol. 325.

Written Opinion in International Application No. PCT/EP2011/050416, Apr. 26, 2011, pp. 1-7.

Written Opinion in International Application No. PCT/EP2011/050413, Apr. 8, 2011, pp. 1-7.

Baba, T. et al. "Construction of Escherichia coli K-12 in-frame, single-gene knockout mutants: the Keio collection" Molecular Systems Biology, 2006, pp. 1-11.

Baneyx, F. et al. "Construction and Characterization of Escherichia coli Strains Deficient in Multiple Secreted Proteases: Protease III Degrades High-Molecular-Weight Substrates In Vivo" Journal of Bacteriology, Apr. 1991, pp. 2696-2703, vol. 173, No. 8.

Spiess, C. et al. "A Temperature-Dependent Switch from Chaperone to Protease in a Widely Conserved Heat Shock Protein" Cell, Apr. 30, 1999, p. 339-347, vol. 97.

Skorko-Glonek, J. et al. "The proteolytic activity of the HtrA (DegP) protein from Escherichia coli at low temperatures" Microbiology, 2008, pp. 3649-3658, vol. 154.

Meerman, H. J. et al. "Construction and Characterization of a Set of E. coli Strains Deficient in All Known Loci Affecting the Proteolytic Stability of Secreted Recombinant Proteins" Bio/Technology, Nov. 1994, pp. 1107-1110, vol. 12.

Written Opinion in International Application No. PCT/GB2010/001790, Feb. 3, 2011, pp. 1-9.

Pending claims from U.S. Appl. No. 14/633,294, 2015, pp. 1-4.

Pending claims from U.S. Appl. No. 14/600,089, 2015, pp. 1-6.

Pending claims from U.S. Appl. No. 14/633,257, 2015, pp. 1-4.

Written Opinion in International Application No. PCT/EP2012/002945, Oct. 24, 2012, pp. 1-9.

Casset, F. et al. "A peptide mimetic of an anti-CD4 monoclonal antibody by rational design" Biochemical and Biophysical Research Communications, 2003, pp. 198-205, vol. 307.

Smith-Gill, S. J. et al. "Contributions of Immunoglobulin Heavy and Light Chains to Antibody Specificity for Lysozyme and Two Haptens" Journal of Immunology, Dec. 15, 1987, pp. 4135-4144, vol. 139.

Song, M.-K. et al. "Light Chain of Natural Antibody Plays a Dominant Role in Protein Antigen Binding" Biochemical and Biophysical Research Communications, 2000, pp. 390-394, vol. 268.

Chen, Y. et al. "Selection and Analysis of an Optimized Anti-VEGF Antibody: Crystal Structure of an Affinity-matured Fab in Complex with Antigen" J. Mol. Biol., 1999, pp. 865-881, vol. 293.

Ward, E. et al. "Binding activities of a repertoire of single immunoglobulin variable domains secreted from Escherichia coli" Nature, Oct. 12, 1989, pp. 544-546, vol. 341.

Kobayashi, H. et al. "Tryptophan H33 plays an important role in pyrimidine (6-4) pyrimidone photoproduct binding by a high-affinity antibody" Protein Engineering, 1999, pp. 879-884, vol. 12, No. 10.

Kumar, S. et al. "Molecular Cloning and Expression of the Fabs of Human Autoantibodies in Escherichia coli" Journal of Biological Chemistry, Nov. 10, 2000, pp. 35129-35136, vol. 275, No. 45.

MacCallum, R. M. et al. "Antibody-antigen Interactions: Contact Analysis and Binding Site Topography" J. Mol. Biol., 1998, pp. 732-745, vol. 262.

Vajdos, F. F. et al. "Comprehensive Functional Maps of the Antigen-binding Site of an Anti-ErbB2 Antibody Obtained with Shotgun Scanning Mutagenesis" J. Mol. Biol., 2002, pp. 415-428, vol. 320.

Colman, P. M. "Effects of amino acid sequence changes on antibody-antigen interactions" Research in Immunology, 1994, pp. 33-36, vol. 145.

(56) References Cited

OTHER PUBLICATIONS

Holm, P. et al. "Functional mapping and single chain construction of the anti-cytokeratin 8 monoclonal antibody TS1" *Molecular Immunology*, 2007, pp. 1075-1084, vol. 44.

Jang, Y.-J. et al. "The structural basis for DNA binding by an anti-DNA autoantibody" *Molecular Immunology*, 1998, pp. 1207-1217, vol. 35.

Wu, H. et al. "Humanization of a Murine Monoclonal Antibody by Simultaneous Optimization of Framework and CDR Residues" *J. Mol. Biol.*, 1999, pp. 151-162, vol. 294.

De Pascalis, R. et al. "Grafting of "Abbreviated" Complementarity-Determining Regions Containing Specificity-Determining Residues Essential for Ligand Contact to Engineer a Less Immunogenic Humanized Monoclonal Antibody" *Journal of Immunology*, 2002, pp. 3076-3084, vol. 169.

Burks, E. A. et al. "In vitro scanning saturation mutagenesis of an antibody binding pocket" *Proc. Natl. Acad. Sci. USA*, Jan. 1997, pp. 412-417, vol. 94.

Brummell, D. A. et al. "Probing the combining site of an anti-carbohydrate antibody by saturation-mutagenesis: role of the heavy-chain CDR3 residues" *Biochemistry*, Feb. 2, 1993, pp. 1180-1187, vol. 32, No. 4.

Brorson, K. et al. "Mutational Analysis of Avidity and Fine Specificity of Anti-Levan Antibodies" *Journal of Immunology*, 1999, pp. 6694-6701, vol. 163.

Rudikoff, S. et al. "Single amino acid substitution altering antigen-binding specificity" *Proc. Natl. Acad. Sci. USA*, Mar. 1982, pp. 1979-1983, vol. 79.

Brams, P. et al. "A humanized anti-human CD154 monoclonal antibody blocks CD154-CD40 mediated human B cell activation" *International Immunopharmacology*, 2001, pp. 277-294, vol. 1.

Boumpas, D.T. et al. "A Short Course of BG9588 (Anti-CD40 Ligand Antibody) Improves Serologic Activity and Decreases Hematuria in Patients With Proliferative Lupus Glomerulonephritis" *Arthritis & Rheumatism*, Mar. 2003, vol. 48, No. 3, pp. 719-727.

Durie, F.H. et al. "Prevention of Collagen-Induced Arthritis with an Antibody to gp39, the Ligand for CD40" *Science*, Sep. 3, 1993, vol. 261, pp. 1328-1330.

Ferrant, J.L. et al. "The contribution of Fc effector mechanisms in the efficacy of anti-CD154 immunotherapy depends on the nature of the immune challenge" *International Immunology*, Oct. 5, 2004, vol. 16, No. 11, pp. 1583-1594.

Kuwana, M. et al. "Effect of a single injection of humanized anti-CD154 monoclonal antibody on the platelet-specific autoimmune response in patients with immune thrombocytopenic purpura" *Blood*, Feb. 15, 2004, vol. 103, No. 4, pp. 1229-1236.

Quezada, S.A. et al. "Distinct Mechanisms of Action of Anti-CD154 in Early Versus Late Treatment of Murine Lupus Nephritis" *Arthritis & Rheumatism*, Sep. 2003, vol. 48, No. 9, pp. 2541-2554.

Kalled, S. L. et al. "Apoptosis and Altered Dendritic Cell Homeostasis in Lupus Nephritis Are Limited by Anti-CD154 Treatment" *The Journal of Immunology*, 2001, pp. 1740-1747, vol. 167.

Cordeiro, A. C. et al. "Novel Therapies in Lupus—Focus on Nephritis" *Acta Reumatol Port.* 2008, pp. 157-169, vol. 33, No. 2.

Toubi, E. et al. "The Role of CD40-CD 154 Interactions in Autoimmunity and the Benefit of Disrupting this Pathway" *Immunity*, 2004, pp. 457-464, vol. 37, Nos. 6-7. Abstract Only.

Peters, A. et al. "CD40 and Autoimmunity: The Dark Side of a Great Activator" *Semin Immunol.*, Oct. 2009, pp. 293-300, vol. 21, No. 5.

Getman, K. et al. "Pharmacokinetic Effects of 4C9, an Anti-FcRn Antibody, in Rats: Implications for the use of FcRn Inhibitors for the Treatment of Humoral Autoimmune and Alloimmune Conditions" *J. Pharm.* 2005, pp. 718-729, vol. 94., No. 4.

Skorko-Glonek, J. et al. "Site-directed mutagenesis of the HtrA(DegP) serine protease, whose proteolytic activity is indispensable for *Escherichia coli* survival at elevated temperatures" *Gene*, 1995, vol. 163, pp. 47-52.

Arbabi-Ghahroudi, M. et al. "Prokaryotic expression of antibodies" *Cancer and Metastasis Reviews*, Dec. 1, 2005, pp. 501-519, vol. 24, No. 4.

Georgiou, G. et al. "Preparative expression of secreted proteins in bacteria: status report and future prospects," *Current Opinion in Biotechnology*, Oct. 1, 2005, pp. 538545, vol. 16, No. 5.

McGraw-Hill, Dictionary of Bioscience, Nov. 12, 1998, pp. 1-3.

Kolaj, O. et al. "Use of folding modulators to improve heterologous protein production in *Escherichia coli*" *Microbial Cell Factories*, 2009, pp. 1-18, vol. 8, No. 9.

Written Opinion in International Application No. PCT/EP2013/059803, Aug. 14, 2013, pp. 1-5.

Hu, Xuejun, et al., "Optimisation of Production of a Domoic Acid-Binding scFv Antibody Fragment in *Escherichia coli* using Molecular Chaperones and Functional Immobilisation on a Mesoporous Silicate Support," Protein Expression and Purification, No. 52, 2007, pp. 194-201.

Hu, Xuejun, et al., "Cloning, Expression and Characterisation of a Single-Chain Fv Antibody Fragment Against Domoic Acid in *Escherichia coli*," Journal of Biotechnology, No. 120, 2005, pp. 38-45.

\* cited by examiner

| Lane | Sample |
|---|---|
| 1 | Molecular Weight Marker |
| 2 | Clarified Extract from MXE008 strain -control (pH6.9) |
| 3 | Clarified Extract from MXE008 strain pH adjustment to 5.0 |
| 4 | Clarified Extract from MXE008 strain pH adjustment to 4.5 |
| 5 | Clarified Extract from MXE008 strain pH adjustment to 3.0 |

Figure 8

SEQ ID NO: 1 shows the amino acid sequence of CDRH1 of CDP870.
Asp Tyr Gly Met Asn SEQ ID NO: 2 shows the amino acid sequence of CDRH2 of CDP870
Trp Ile Asn Thr Tyr Ile Gly Glu Pro Ile Tyr Ala Asp Ser Val Lys Gly SEQ ID NO: 3 shows the amino acid sequence of CDRH3 of CDP870.
Gly Tyr Arg Ser Tyr Ala Met Asp Tyr SEQ ID NO: 4 shows the amino acid sequence of CDRL1 of CDP870.
Lys Ala Ser Gln Asn Val Gly Thr Asn Val Ala SEQ ID NO: 5 shows the amino acid sequence of CDRL2 of CDP870.
Ser Ala Ser Phe Leu Tyr Ser SEQ ID NO: 6 shows the amino acid sequence of CDRL3 of CDP870.
Gln Gln Tyr Asn Ile Tyr Pro Leu Thr SEQ ID NO: 7 shows the amino acid sequence of the light chain variable region CDP870
Asp Ile Gln Met Thr Gln Ser Pro Ser Ser Leu Ser Ala Ser Val Gly Asp Arg Val Thr Ile Thr Cys Lys Ala Ser Gln Asn Val Gly Thr Asn Val Ala Trp Tyr Gln Gln Lys Pro Gly Lys Ala Pro Lys Ala Leu Ile Tyr Ser Ala Ser Phe Leu Tyr Ser Gly Val Pro Tyr Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Tyr Asn Ile Tyr Pro Leu Thr Phe Gly Gln Gly Thr Lys Val Glu Ile Lys

Figure 8 (continued)

SEQ ID NO:8 shows the amino acid sequence of the heavy chain variable region CDP870.
Glu Val Gln Leu Val Glu Ser Gly Gly Gly Leu Val Gln Pro Gly Gly Ser Leu Arg Leu Ser
Cys Ala Ala Ser Gly Tyr Val Phe Thr Asp Tyr Gly Met Asn Trp Val Arg Gln Ala Pro
Gly Lys Gly Leu Glu Trp Met Gly Trp Ile Asn Thr Tyr Ile Gly Glu Pro Ile Tyr Ala Asp
Ser Val Lys Gly Arg Phe Thr Phe Ser Leu Asp Thr Ser Lys Ser Thr Ala Tyr Leu Gln Met
Asn Ser Leu Arg Ala Glu Asp Thr Ala Val Tyr Tyr Cys Ala Arg Gly Tyr Arg Ser Tyr
Ala Met Asp Tyr Trp Gly Gln Gly Thr Leu Val Thr Val Ser Ser SEQ ID NO: 9 shows the amino acid sequence of a grafted anti-TNFα Fab CDP870 light chain.
Asp Ile Gln Met Thr Gln Ser Pro Ser Ser Leu Ser Ala Ser Val Gly Asp Arg Val Thr Ile
Thr Cys Lys Ala Ser Gln Asn Val Gly Thr Asn Val Ala Trp Tyr Gln Gln Lys Pro Gly
Lys Ala Pro Lys Ala Leu Ile Tyr Ser Ala Ser Phe Leu Tyr Ser Gly Val Pro Tyr Arg Phe
Ser Gly Ser Gly Ser Gly Thr Asp Phe Thr Leu Thr Ile Ser Ser Leu Gln Pro Glu Asp Phe
Ala Thr Tyr Tyr Cys Gln Gln Tyr Asn Ile Tyr Pro Leu Thr Phe Gly Gln Gly Thr Lys Val
Glu Ile Lys Arg Thr Val Ala Ala Pro Ser Val Phe Ile Phe Pro Pro Ser Asp Glu Gln Leu
Lys Ser Gly Thr Ala Ser Val Val Cys Leu Leu Asn Asn Phe Tyr Pro Arg Glu Ala Lys
Val Gln Trp Lys Val Asp Asn Ala Leu Gln Ser Gly Asn Ser Gln Glu Ser Val Thr Glu
Gln Asp Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val Thr Lys
Ser Phe Asn Arg Gly Glu Cys

Figure 8 (continued)

SEQ ID NO: 10 shows the amino acid sequence of a grafted anti-TNFα Fab CDP870 heavy chain.

Glu Val Gln Leu Val Glu Ser Gly Gly Gly Leu Val Gln Pro Gly Gly Ser Leu Arg Leu Ser Cys Ala Ala Ser Gly Tyr Val Phe Thr Asp Tyr Gly Met Asn Trp Val Arg Gln Ala Pro Gly Lys Gly Leu Glu Trp Met Gly Trp Ile Asn Thr Tyr Ile Gly Glu Pro Ile Tyr Ala Asp Ser Val Lys Gly Arg Phe Thr Phe Ser Leu Asp Thr Ser Lys Ser Thr Ala Tyr Leu Gln Met Asn Ser Leu Arg Ala Glu Asp Thr Ala Val Tyr Tyr Cys Ala Arg Gly Tyr Arg Ser Tyr Ala Met Asp Tyr Trp Gly Gln Gly Thr Leu Val Thr Val Ser Ser Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Ala Ala

SEQ ID NO: 11 is the nucleotide sequence of his-tagged DsbC.

```
atgaagaaag gtttatgtt gtttactttg ttagcggcgt tttcaggctt tgctcaggct      60
gatgacgcgg caattcaaca aacgttagcc aaaatgggca tcaaaagcag cgatattcag    120
ccgcgcctg tagctggcat gaagacagtt ctgactaaca gcggcgtgtt gtacatcacc     180
gatgatggta aacatatcat tcagggcca atgtatgacg ttagtggcac ggctccggtc     240
aatgtcacca ataagatgct gttaaagcag ttgaatgcgc ttgaaaaaga gatgatcgtt    300
tataaagcgc cgcaggaaaa acacgtcatc accgtgttta ctgatattac ctgtggttac    360
tgccacaaac tgcatgagca aatggcagac tacaacgcgc tggggatcac cgtgcgttat    420
cttgctttcc cgcgccaggg gctggacagc gatgcagaga agaaatgaa agctatctgg    480
tgtgcgaaag ataaaaacaa agcgtttgat gatgtgatgg caggtaaaag cgtcgcacca    540
gccagttgcg acgtggatat tgccgaccat tacgcacttg gcgtccagct tggcgttagc    600
ggtactccgg cagttgtgct gagcaatggc acacttgttc cgggttacca gccgcgaaa    660
gagatgaaag aatttctcga cgaacaccaa aaaatgacca gcggtaaaca ccatcaccat    720
```

Figure 8 (continued)

SEQ ID NO: 12 is the amino acid sequence of his-tagged DsbC.

```
MKKGFMLFTL LAAFSGFAQA DDAAIQQTLA KMGIKSSDIQ PAPVAGMKTV LTNSGVLYIT
DDGKHIIQGP MYDVSGTAPV NVTNKMLLKQ LNALEKEMIV YKAPQEKHVI TVFTDITCGY
CHKLHEQMAD YNALGITVRY LAFPRQGLDS DAEKEMKAIW CAKDKNKAFD DVMAGKSVAP
ASCDVDIADH YALGVQLGVS GTPAVVLSNG TLVPGYQPPK EMKEFLDEHQ KMTSGKHHHH
HH
```

SEQ ID NO: 13 is the sequence of the wild-type spr gene including the signal sequence which is the first 26 amino acid residues Met Val Lys Ser Gln Pro Ile Leu Arg Tyr Ile Leu Arg Gly Ile Pro Ala Ile Ala Val Ala
Val Leu Leu Ser Ala Cys Ser Ala Asn Asn Thr Ala Lys Asn Met His Pro Glu Thr Arg
Ala Val Gly Ser Glu Thr Ser Ser Leu Gln Ala Ser Gln Asp Glu Phe Glu Asn Leu Val Arg
Asn Val Asp Val Lys Ser Arg Ile Met Asp Gln Tyr Ala Asp Trp Lys Gly Val Arg Tyr
Arg Leu Gly Gly Ser Thr Lys Lys Gly Ile Asp Cys Ser Gly Phe Val Gln Arg Thr Phe Arg
Glu Gln Phe Gly Leu Glu Leu Pro Arg Ser Thr Tyr Glu Gln Gln Glu Met Gly Lys Ser
Val Ser Arg Ser Asn Leu Arg Thr Gly Asp Leu Val Leu Phe Arg Ala Gly Ser Thr Gly
Arg His Val Gly Ile Tyr Ile Gly Asn Asn Gln Phe Val His Ala Ser Thr Ser Ser Gly Val
Ile Ile Ser Ser Met Asn Glu Pro Tyr Trp Lys Lys Arg Tyr Asn Glu Ala Arg Arg Val Leu
Ser Arg Ser SEQ ID NO: 14 is the sequence of the wild-type spr gene without the signal sequence.
Cys Ser Ala Asn Asn Thr Ala Lys Asn Met His Pro Glu Thr Arg Ala Val Gly Ser Glu
Thr Ser Ser Leu Gln Ala Ser Gln Asp Glu Phe Glu Asn Leu Val Arg Asn Val Asp Val
Lys Ser Arg Ile Met Asp Gln Tyr Ala Asp Trp Lys Gly Val Arg Tyr Arg Leu Gly Gly Ser
Thr Lys Lys Gly Ile Asp Cys Ser Gly Phe Val Gln Arg Thr Phe Arg Glu Gln Phe Gly
Leu Glu Leu Pro Arg Ser Thr Tyr Glu Gln Gln Glu Met Gly Lys Ser Val Ser Arg Ser Asn
Leu Arg Thr Gly Asp Leu Val Leu Phe Arg Ala Gly Ser Thr Gly Arg His Val Gly Ile Tyr
Ile Gly Asn Asn Gln Phe Val His Ala Ser Thr Ser Ser Gly Val Ile Ile Ser Ser Met Asn
Glu Pro Tyr Trp Lys Lys Arg Tyr Asn Glu Ala Arg Arg Val Leu Ser Arg Ser

Figure 8 (continued)

SEQ ID NO: 15 is the DNA sequence of a mutated knockout Tsp gene including the 6 nucleotides ATGAAT upstream of the start codon.

| | |
|---|---|
| atgaattcgt ttttaggctt accgcgttag ctggcctgct tgcaatagca ggccagacat | 60 |
| taattgtaga agatatcacg cgtgctgatc aaattccggt attaaaggaa gagacgcagc | 120 |
| atgcgacggt aagtgagcgc gtaacgtcgc gcttcacccg ttctcattat cgccagttcg | 180 |
| acctcgatca ggcattttcg gccaaaatct ttgaccgcta cctgaatctg ctcgattaca | 240 |
| gccacaacgt gctgctggca agcgatgttg aacagttcgc gaaaaagaaa accgagttag | 300 |
| gcgatgaact gcgttcaggc aaaactcgacg ttttctacga tctctacaat ctggcgcaaa | 360 |
| agcgccgttt tgagcgttac cagtacgctt tgtcggtact ggaaaagccg atggatttca | 420 |
| ccggcaacga cacttataac cttgaccgca gcaaagcgcc ctggccgaaa aacgaggctg | 480 |
| agttgaacgc gctgtgggac agtaaagtca aattcgacga gttaagcctg aagctgacag | 540 |
| gaaaaacgga taaagaaatt cgtgaaaccc tgactcgccg ctacaaattt gccattcgtc | 600 |
| gtctggcgca aaccaacagc gaagatgttt tctcgctggc aatgacggcg tttgcgcgtg | 660 |
| aaatcgaccc gcataccaac tatctttccc cgcgtaatac cgaacagttc aacactgaaa | 720 |
| tgagtttgtc gctggaaggt attggcgcag tgctgcaaat ggatgatgac tacaccgtta | 780 |
| tcaattcgat ggtggcaggt ggtccggcag cgaagagtaa agctatcagc gttggtgaca | 840 |
| aaattgtcgg tgttggtcaa acaggcaagc cgatggttga cgtgattggc tggcgtcttg | 900 |
| atgatgtggt tgccttaatt aaagggccga agggcagtaa agttcgtctg gaaattttac | 960 |
| ctgctggtaa agggaccaag acccgtactg taacgttgac ccgtgaacgt attcgtctcg | 1020 |
| aagaccgcgc ggttaaaatg tcggtgaaga ccgtcggtaa agagaaagtc ggcgtgctgg | 1080 |
| atattccggg cttctatgtg ggtttgacag acgatgtcaa agtgcaactg cagaaactgg | 1140 |
| aaaaacagaa tgtcagcagc gtcatcatcg acctgcgtag caatggcggt ggggcgttaa | 1200 |
| ctgaagccgt atcgctctcc ggtctgttta ttcctgcggg tcccattgtt caggtccgcg | 1260 |
| ataacaacgg caaggttcgt gaagatagcg ataccgacgg acaggttttc tataaaggcc | 1320 |
| cgctggtggt gctggttgac cgcttcagtg cttcggcttc agaaatcttt gccgcggcaa | 1380 |
| tgcaggatta cggtcgtgcg ctggttgtgg gtgaaccgac gtttggtaaa ggcaccgttc | 1440 |
| agcaataccg ttcattgaac cgtatttacg atcagatgtt acgtcctgaa tggccagcgc | 1500 |
| tgggttctgt gcagtacacg atccagaaat tctatcgcgt taacggcggc agtacgcaac | 1560 |

Figure 8 (continued)

gtaaaggcgt aacgccagac atcatcatgc cgacgggtaa tgaagaaacg gaaacgggtg    1620
agaaattcga agataacgcg ctgccgtggg atagcattga tgccgcgact tatgtgaaat    1680
caggagattt aacggccttt gaaccggagc tgctgaagga acataatgcg cgtatcgcga    1740
aagatcctga gttccagaac atcatgaagg atatcgcgcg cttcaacgct atgaaggaca    1800
agcgcaatat cgtttctctg aattacgctg tgcgtgagaa agagaataat gaagatgatg    1860
cgacgcgtct ggcgcgtttg aacgaacgct ttaaacgcga aggtaaaccg gagttgaaga    1920
aactggatga tctaccgaaa gattaccagg agccggatcc ttatctggat gagacggtga    1980
atatcgcact cgatctggcg aagcttgaaa aagccagacc cgcggaacaa cccgctcccg    2040
tcaagtaa                                                              2048

SEQ ID NO: 16 shows the oligonucleotide cassette encoding intergenic sequence 2 (IGS2) for *E. coli* Fab expression.

gagctcacca gtaacaaaaa gttttaatag aggggagtgt taaaatgaag aagactgcta    60
tagcaattg                                                              69

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial
<220> FEATURE:
<223> OTHER INFORMATION: Amino acid sequence of CDRH1 of CDP870

<400> SEQUENCE: 1

Asp Tyr Gly Met Asn
1               5

<210> SEQ ID NO 2
<211> LENGTH: 17
<212> TYPE: PRT
<213> ORGANISM: Artificial
<220> FEATURE:
```

<223> OTHER INFORMATION: Amino acid sequence of CDRH2 of CDP870

<400> SEQUENCE: 2

```
Trp Ile Asn Thr Tyr Ile Gly Glu Pro Ile Tyr Ala Asp Ser Val Lys
1               5                   10                  15
Gly
```

<210> SEQ ID NO 3
<211> LENGTH: 9
<212> TYPE: PRT
<213> ORGANISM: Artificial
<220> FEATURE:
<223> OTHER INFORMATION: Amino acid sequence of CDRH3 of CDP870

<400> SEQUENCE: 3

```
Gly Tyr Arg Ser Tyr Ala Met Asp Tyr
1               5
```

<210> SEQ ID NO 4
<211> LENGTH: 11
<212> TYPE: PRT
<213> ORGANISM: Artificial
<220> FEATURE:
<223> OTHER INFORMATION: Amino acid sequence of CDRL1 of CDP870

<400> SEQUENCE: 4

```
Lys Ala Ser Gln Asn Val Gly Thr Asn Val Ala
1               5                   10
```

<210> SEQ ID NO 5
<211> LENGTH: 7
<212> TYPE: PRT
<213> ORGANISM: Artificial
<220> FEATURE:
<223> OTHER INFORMATION: Amino acid sequence of CDRL2 of CDP870

<400> SEQUENCE: 5

```
Ser Ala Ser Phe Leu Tyr Ser
1               5
```

<210> SEQ ID NO 6
<211> LENGTH: 9
<212> TYPE: PRT
<213> ORGANISM: Artificial
<220> FEATURE:
<223> OTHER INFORMATION: Amino acid sequence of CDRL3 of CDP870

<400> SEQUENCE: 6

```
Gln Gln Tyr Asn Ile Tyr Pro Leu Thr
1               5
```

<210> SEQ ID NO 7
<211> LENGTH: 107
<212> TYPE: PRT
<213> ORGANISM: Artificial
<220> FEATURE:
<223> OTHER INFORMATION: Amino acid sequence of the light chain variable
      region CDP870

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
```

```
                35                  40                  45
Tyr Ser Ala Ser Phe Leu Tyr Ser Gly Val Pro Tyr Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ile Tyr Pro Leu
                85                  90                  95
Thr Phe Gly Gln Gly Thr Lys Val Glu Ile Lys
            100                 105

<210> SEQ ID NO 8
<211> LENGTH: 118
<212> TYPE: PRT
<213> ORGANISM: Artificial
<220> FEATURE:
<223> OTHER INFORMATION: Amino acid sequence of the heavy chain variable
      region CDP870

<400> SEQUENCE: 8

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Val Phe Thr Asp Tyr
            20                  25                  30
Gly Met Asn Trp Val Arg Gln Ala Pro Gly Lys Gly Leu Glu Trp Met
        35                  40                  45
Gly Trp Ile Asn Thr Tyr Ile Gly Glu Pro Ile Tyr Ala Asp Ser Val
    50                  55                  60
Lys Gly Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Arg Gly Tyr Arg Ser Tyr Ala Met Asp Tyr Trp Gly Gln Gly Thr
            100                 105                 110
Leu Val Thr Val Ser Ser
        115

<210> SEQ ID NO 9
<211> LENGTH: 214
<212> TYPE: PRT
<213> ORGANISM: Artificial
<220> FEATURE:
<223> OTHER INFORMATION: Amino acid sequence of a grafted anti-TNF? Fab
      CDP870 light chain

<400> SEQUENCE: 9

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Val Gly Thr Asn
            20                  25                  30
Val Ala Trp Tyr Gln Gln Lys Pro Gly Lys Ala Pro Lys Ala Leu Ile
        35                  40                  45
Tyr Ser Ala Ser Phe Leu Tyr Ser Gly Val Pro Tyr Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ile Tyr Pro Leu
                85                  90                  95
Thr Phe Gly Gln Gly Thr Lys Val Glu Ile Lys Arg Thr Val Ala Ala
```

```
                  100                 105                 110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 10
<211> LENGTH: 229
<212> TYPE: PRT
<213> ORGANISM: Artificial
<220> FEATURE:
<223> OTHER INFORMATION: Amino acid sequence of a grafted anti-TNF? Fab
      CDP870 heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225
```

<210> SEQ ID NO 11
<211> LENGTH: 720
<212> TYPE: DNA
<213> ORGANISM: Artificial
<220> FEATURE:
<223> OTHER INFORMATION: Nucleotide sequence of his-tagged DsbC

<400> SEQUENCE: 11

```
atgaagaaag gttttatgtt gtttactttg ttagcggcgt tttcaggctt tgctcaggct      60
gatgacgcgg caattcaaca aacgttagcc aaaatgggca tcaaaagcag cgatattcag     120
cccgcgcctg tagctggcat gaagacagtt ctgactaaca gcggcgtgtt gtacatcacc     180
gatgatggta acatatcat tcaggggcca atgtatgacg ttagtggcac ggctccggtc      240
aatgtcacca ataagatgct gttaaagcag ttgaatgcgc ttgaaaaaga gatgatcgtt     300
tataaagcgc cgcaggaaaa acacgtcatc accgtgttta ctgatattac ctgtggttac     360
tgccacaaac tgcatgagca atggcagac tacaacgcgc tggggatcac cgtgcgttat      420
cttgctttcc cgcgccaggg gctggacagc gatgcagaga agaaaatgaa agctatctgg     480
tgtgcgaaag ataaaaacaa agcgtttgat gatgtgatgg caggtaaaag cgtcgcacca     540
gccagttgcg acgtggatat tgccgaccat tacgcacttg cgtccagct tggcgttagc      600
ggtactccgg cagttgtgct gagcaatggc acacttgttc cgggttacca gccgccgaaa     660
gagatgaaag aatttctcga cgaacaccaa aaaatgacca gcggtaaaca ccatcaccat     720
```

<210> SEQ ID NO 12
<211> LENGTH: 242
<212> TYPE: PRT
<213> ORGANISM: Artificial
<220> FEATURE:
<223> OTHER INFORMATION: Amino acid sequence of his-tagged DsbC

<400> SEQUENCE: 12

```
Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
                20                  25                  30

Gly Ile Lys Ser Ser Asp Ile Gln Pro Ala Pro Val Ala Gly Met Lys
            35                  40                  45

Thr Val Leu Thr Asn Ser Gly Val Leu Tyr Ile Thr Asp Asp Gly Lys
        50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
                100                 105                 110

Phe Thr Asp Ile Thr Cys Gly Tyr Cys His Lys Leu His Glu Gln Met
            115                 120                 125

Ala Asp Tyr Asn Ala Leu Gly Ile Thr Val Arg Tyr Leu Ala Phe Pro
        130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190
```

```
Leu Gly Val Gln Leu Gly Val Ser Gly Thr Pro Ala Val Val Leu Ser
        195                 200                 205

Asn Gly Thr Leu Val Pro Gly Tyr Gln Pro Pro Lys Glu Met Lys Glu
        210                 215                 220

Phe Leu Asp Glu His Gln Lys Met Thr Ser Gly Lys His His His His
225                 230                 235                 240

His His

<210> SEQ ID NO 13
<211> LENGTH: 188
<212> TYPE: PRT
<213> ORGANISM: Artificial
<220> FEATURE:
<223> OTHER INFORMATION: Amino acid sequence of wild-type spr gene
      including the signal sequence which is the first 26 amino acid
      residues

<400> SEQUENCE: 13

Met Val Lys Ser Gln Pro Ile Leu Arg Tyr Ile Leu Arg Gly Ile Pro
1               5                   10                  15

Ala Ile Ala Val Ala Val Leu Leu Ser Ala Cys Ser Ala Asn Asn Thr
            20                  25                  30

Ala Lys Asn Met His Pro Glu Thr Arg Ala Val Gly Ser Glu Thr Ser
        35                  40                  45

Ser Leu Gln Ala Ser Gln Asp Glu Phe Glu Asn Leu Val Arg Asn Val
    50                  55                  60

Asp Val Lys Ser Arg Ile Met Asp Gln Tyr Ala Asp Trp Lys Gly Val
65                  70                  75                  80

Arg Tyr Arg Leu Gly Gly Ser Thr Lys Lys Gly Ile Asp Cys Ser Gly
                85                  90                  95

Phe Val Gln Arg Thr Phe Arg Glu Gln Phe Gly Leu Glu Leu Pro Arg
            100                 105                 110

Ser Thr Tyr Glu Gln Gln Glu Met Gly Lys Ser Val Ser Arg Ser Asn
        115                 120                 125

Leu Arg Thr Gly Asp Leu Val Leu Phe Arg Ala Gly Ser Thr Gly Arg
    130                 135                 140

His Val Gly Ile Tyr Ile Gly Asn Asn Gln Phe Val His Ala Ser Thr
145                 150                 155                 160

Ser Ser Gly Val Ile Ile Ser Ser Met Asn Glu Pro Tyr Trp Lys Lys
                165                 170                 175

Arg Tyr Asn Glu Ala Arg Arg Val Leu Ser Arg Ser
            180                 185

<210> SEQ ID NO 14
<211> LENGTH: 162
<212> TYPE: PRT
<213> ORGANISM: Artificial
<220> FEATURE:
<223> OTHER INFORMATION: Amino acid sequence of the wild-type spr gene
      without the signal sequence

<400> SEQUENCE: 14

Cys Ser Ala Asn Asn Thr Ala Lys Asn Met His Pro Glu Thr Arg Ala
1               5                   10                  15

Val Gly Ser Glu Thr Ser Ser Leu Gln Ala Ser Gln Asp Glu Phe Glu
            20                  25                  30

Asn Leu Val Arg Asn Val Asp Val Lys Ser Arg Ile Met Asp Gln Tyr
        35                  40                  45
```

```
Ala Asp Trp Lys Gly Val Arg Tyr Arg Leu Gly Gly Ser Thr Lys Lys
     50                  55                  60

Gly Ile Asp Cys Ser Gly Phe Val Gln Arg Thr Phe Arg Glu Gln Phe
 65                  70                  75                  80

Gly Leu Glu Leu Pro Arg Ser Thr Tyr Glu Gln Gln Glu Met Gly Lys
                 85                  90                  95

Ser Val Ser Arg Ser Asn Leu Arg Thr Gly Asp Leu Val Leu Phe Arg
             100                 105                 110

Ala Gly Ser Thr Gly Arg His Val Gly Ile Tyr Ile Gly Asn Asn Gln
         115                 120                 125

Phe Val His Ala Ser Thr Ser Ser Gly Val Ile Ile Ser Ser Met Asn
     130                 135                 140

Glu Pro Tyr Trp Lys Lys Arg Tyr Asn Glu Ala Arg Arg Val Leu Ser
145                 150                 155                 160

Arg Ser

<210> SEQ ID NO 15
<211> LENGTH: 2048
<212> TYPE: DNA
<213> ORGANISM: Artificial
<220> FEATURE:
<223> OTHER INFORMATION: DNA sequence of a mutated knockout Tsp gene
      including the 6 nucleotides ATGAAT upstream of the start codon

<400> SEQUENCE: 15
atgaattcgt ttttaggctt accgcgttag ctggcctgct tgcaatagca ggccagacat      60
taattgtaga agatatcacg cgtgctgatc aaattccggt attaaaggaa gagacgcagc     120
atgcgacggt aagtgagcgc gtaacgtcgc gcttcacccg ttctcattat cgccagttcg     180
acctcgatca ggcattttcg gccaaaatct ttgaccgcta cctgaatctg ctcgattaca     240
gccacaacgt gctgctggca agcgatgttg aacagttcgc gaaaaagaaa accgagttag     300
gcgatgaact gcgttcaggc aaactcgacg ttttctacga tctctacaat ctggcgcaaa     360
agcgccgttt tgagcgttac cagtacgctt tgtcggtact ggaaaagccg atggatttca     420
ccggcaacga cacttataac cttgaccgca gcaaagcgcc ctggccgaaa aacgaggctg     480
agttgaacgc gctgtgggac agtaaagtca aattcgacga gttaagcctg aagctgacag     540
gaaaaacgga taagaaaatt cgtgaaaccc tgactcgccg ctacaaattt gccattcgtc     600
gtctggcgca aaccaacagc gaagatgttt tctcgctggc aatgacggcg tttgcgcgtg     660
aaatcgaccc gcataccaac tatctttccc cgcgtaatac cgaacagttc aacactgaaa     720
tgagtttgtc gctggaaggt attggcgcag tgctgcaaat ggatgatgac tacaccgtta     780
tcaattcgat ggtggcaggt ggtccggcag cgaagagtaa agctatcagc gttggtgaca     840
aaattgtcgg tgttggtcaa acaggcaagc cgatggttga cgtgattggc tggcgtcttg     900
atgatgtggt tgccttaatt aaagggccga agggcagtaa agttcgtctg gaaattttac     960
ctgctggtaa agggaccaag accgtactg taacgttgac ccgtgaacgt attcgtctcg    1020
aagaccgcgc ggttaaaatg tcggtgaaga ccgtcggtaa agagaaagtc ggcgtgctgg    1080
atattccggg cttctatgtg ggtttgcag acgatgtcaa agtgcaactg cagaaactgg    1140
aaaaacagaa tgtcagcagc gtcatcatcg acctgcgtag caatggcggt ggggcgttaa    1200
ctgaagcccg atcgctctcc ggtctgtttta ttcctgcggg tcccattgtt caggtccgcg    1260
ataacaacgg caaggttcgt gaagatagcg ataccgacgg acaggttttc tataaaggcc    1320
```

```
cgctggtggt gctggttgac cgcttcagtg cttcggcttc agaaatcttt gccgcggcaa    1380
tgcaggatta cggtcgtgcg ctggttgtgg gtgaaccgac gtttggtaaa ggcaccgttc    1440
agcaataccg ttcattgaac cgtatttacg atcagatgtt acgtcctgaa tggccagcgc    1500
tgggttctgt gcagtacacg atccagaaat tctatcgcgt taacggcggc agtacgcaac    1560
gtaaaggcgt aacgccagac atcatcatgc cgacgggtaa tgaagaaacg gaaacgggtg    1620
agaaattcga agataacgcg ctgccgtggg atagcattga tgccgcgact tatgtgaaat    1680
caggagattt aacggccttt gaaccggagc tgctgaagga acataatgcg cgtatcgcga    1740
aagatcctga gttccagaac atcatgaagg atatcgcgcg cttcaacgct atgaaggaca    1800
agcgcaatat cgtttctctg aattacgctg tgcgtgagaa agagaataat gaagatgatg    1860
cgacgcgtct ggcgcgtttg aacgaacgct ttaaacgcga aggtaaaccg gagttgaaga    1920
aactggatga tctaccgaaa gattaccagg agccggatcc ttatctggat gagacggtga    1980
atatcgcact cgatctggcg aagcttgaaa aagccagacc cgcggaacaa cccgctcccg    2040
tcaagtaa                                                             2048

<210> SEQ ID NO 16
<211> LENGTH: 69
<212> TYPE: DNA
<213> ORGANISM: Artificial
<220> FEATURE:
<223> OTHER INFORMATION: Oligonucleotide cassette encoding intergenic
      sequence 2 (IGS2) for E. coli Fab expression

<400> SEQUENCE: 16
gagctcacca gtaacaaaaa gttttaatag aggggagtgt taaaatgaag aagactgcta    60
tagcaattg                                                            69
```

PROCESS FOR PURIFYING PROTEINS

This application is a national phase entry of International Application No. PCT/GB2011/001129, filed Jul. 27, 2011, which claims the benefit of Great Britain Application No. 1012599.5, filed Jul. 27, 2010.

This invention relates to a process for purifying a recombinant protein from a gram-negative host cell sample or extract thereof. More particularly, the gram-negative host cell sample or extract thereof is adjusted to a low pH to effect the precipitation of protein disulphide isomerase.

Recombinant DNA techniques have rapidly developed and are useful in the production of antibodies, in particular therapeutic antibodies. Systems for the expression of recombinant genes are well known to the person skilled in the field in question. These include expression in mammalian cells, insect cells, fungal cells, bacterial cells and transgenic animals and plants. The choice of expression system is dependent on the features of the encoded protein, for example post-translational modifications. Other considerations include the time and, in particular, the cost involved in the production of the desired quantity of material of the required quality. These latter considerations are particularly important in the production of therapeutic antibodies of the quality required for regulatory approval and in the quantities needed for treatment of large numbers of patients.

A widely used system for the production of recombinant proteins is based on expression in *Escherichia coli* (*E. coli*). A specific problem encountered with the use of *E. coli* is the difficulty in producing material of the required quality in quantities needed for therapy. In particular, the time and costs involved can be prohibitive. One specific problem of note is the loss incurred in the yield of antibodies during purification of the antibodies from *E. coli*.

Although, proportionally, the purification costs are a fraction of the total cost of a therapeutic antibody product, the purification cost proportion will increase further as upstream production costs become cheaper. Thus, improvements in recovery and purification of antibodies will drive production costs down further irrespective of the means of production (Humphreys & Glover, Curr. Opin. Drug Discovery & Development, 2001, 4:172-185), Hence, there is a need for methods that introduce time and/or cost savings into therapeutic antibody production and, in particular, in purification, for example by increasing product recovery and/or improving the quality of the product stream.

Low product yield is often a particular problem noted during the downstream purification steps. A specific problem in downstream purification concerns the separation of host cell proteins (HCP) which are released upon extraction of the therapeutic antibody from the host cell. A number of process modifications have been tried in order to address this problem. Examples of such processes include the following:

The protein of interest may be precipitated and then separated from other HCP contaminants. However, the precipitation of a therapeutic antibody may cause irreversible damage to the antibody. Techniques that specifically precipitate the protein of interest often result in the entrapment of the non-proteinaceous contaminants in the precipitate, rendering the separation ineffective.

Alternatively, the HCP may be precipitated away from the therapeutic antibody. U.S. Pat. No. 7,169,908 describes the addition of a solution of ethacridine lactate to precipitate host cell impurities. However, the use of an agent such as ethacridine lactate is not suitable for the production of therapeutic proteins because it has been used as an abortion agent and may be harmful to the patient if it is not completely removed. The HCPs from a CHO cell culture have been precipitated using a small molecule and pH adjustment in order to purify a protein (Arunakumari A. et al. Advances in Non-Protein A Purification Processes for Human Monoclonal Antibodies Supplement to BioPharm International March 2009 p 22-26).

Whilst such methods have contributed to helping to purifying therapeutic antibodies from host cell contaminants there is still a need to provide improved methods to reduce the quantity of HCPs from microbial host cell systems without negatively affecting the properties of the therapeutic antibody in order to facilitate further downstream processing.

What is more the inventors have found that the expression of certain chaperone proteins, for example a disulfide isomerase, such as DsbC, by the host can be useful in increasing the levels of expression of antibodies or fragments thereof. However, the chaperone protein is expressed at significant levels and becomes a large by-product of the process that requires removal.

Removing large amounts of contaminant can be challenging because methods such as column chromatography find it difficult to remove large amounts of a protein contaminant due to column fowling and the need to use large amounts of reagents or solvents.

When isolated DsbC is tested it is soluble at low pHs such as pH 3. However, the present inventors have surprisingly found that pH adjustment of 5 or less may be used to precipitate recombinant disulphide isomerase from a gram-negative bacterial host cell and thereby facilitate further processing of a recombinant protein of interest, such as a therapeutic antibody.

SUMMARY OF THE INVENTION

In one aspect there is provided a method for purifying a recombinant protein from a host cell, for example a gram-negative bacterial host cell sample expressing a recombinant protein and a recombinant disulphide isomerase or extract thereof; comprising:
  a. adjusting the pH of the host cell sample or extract thereof to a pH of 5 or less to precipitate the recombinant disulphide isomerase; and
  b. separating precipitated recombinant disulphide isomerase from the recombinant protein to provide a recombinant protein sample.

The present invention also provides the use of a step of adjusting the pH of a gram-negative bacterial host cell sample transformed with an expression vector encoding a recombinant protein or extract thereof to a pH of 5 or less to precipitate host cell recombinant disulphide isomerase, followed by separation of the precipitated host cell recombinant disulphide isomerase from the recombinant protein and provide a purified recombinant protein sample.

In one embodiment there is provided a method for purifying a recombinant antibody or a binding fragment thereof from a gram-negative bacterial host cell sample or an extract of said host cell wherein said host cells expresses the recombinant antibody or binding fragment thereof and a recombinant disulphide isomerase DsbC; wherein the method comprises:
  a. adjusting the pH of the host cell sample or extract thereof to a pH in the range 3.5 to 5 to precipitate the recombinant DsbC; and
  b. separating precipitated recombinant DsbC to provide a sample containing a purified recombinant antibody or fragment thereof.

Surprisingly this pH adjustment step precipitates a significant quantity of the host cell recombinant disulphide isomerase from the solution and thereby allows separation of the host cell recombinant disulphide isomerase from the recombinant protein of interest. This facilitates downstream processing, particularly any subsequent chromatography steps such as non-affinity chromatography capture, by reducing the host cell disulphide isomerase in the solution competing with the recombinant protein for binding sites on the chromatography column. Therefore, the load of HCPs on the chromatography column is minimized and yield of the recombinant protein of interest is improved when the same size and number of chromatography columns are used. This reduces the time and cost of further downstream purification.

Interestingly pure DsbC does not precipitate at a pH in the range 3.0 to 5 (see FIG. 4). However, when present in the complex environment of a gram-negative cell expressing an antibody or a binding fragment thereof or alternatively in the presence of part or all of the contents of the said cells then the DsbC precipitates. Whilst not wishing to be bound by theory it is hypothesized that the complex matrix environment of the host cell or extract therefrom catalyzes the precipitation of the disulphide isomerase, such as DsbC, in the pH range even though normally the protein is soluble at a pH in the range 3.5 to 5. Perhaps once the precipitation is initiated it continues and escalates.

Thus, the method according to the present disclosure is suitable for use on large scales and therefore is very useful in commercial processing of proteins such as antibodies.

BRIEF DESCRIPTION OF THE DRAWINGS

FIG. 8 shows sequences SEQ ID NOs: 1 to 16.

BRIEF DESCRIPTION OF THE SEQUENCES

Figure 1:
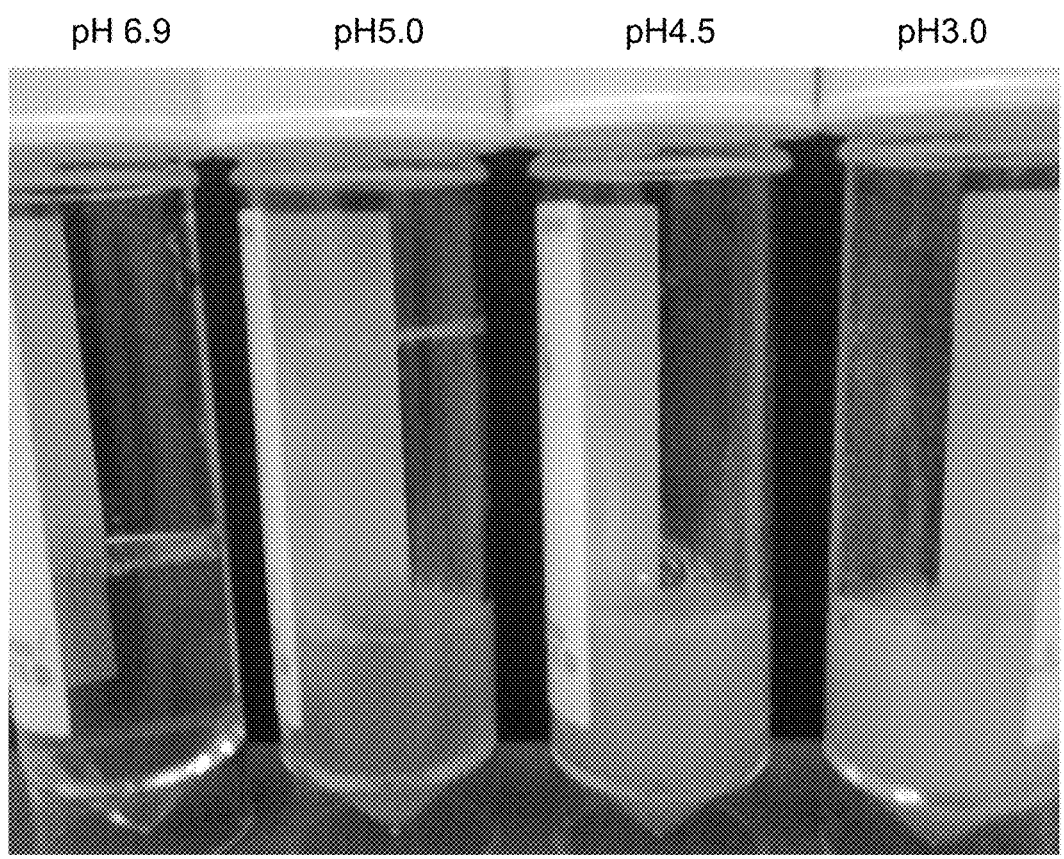
FIG. 1 shows the observed precipitation of the host cell solution after the pH has been adjusted to pH 5.0, pH 4.5 or pH 3.0 compared to the control pH of 6.9.

SEQ ID NO: 1 shows the amino acid sequence of CDRH1 of CDP870.

SEQ ID NO: 2 shows the amino acid sequence of CDRH2 of CDP870.

SEQ ID NO: 3 shows the amino acid sequence of CDRH3 of CDP870.

SEQ ID NO: 4 shows the amino acid sequence of CDRL1 of CDP870.

SEQ ID NO: 5 shows the amino acid sequence of CDRL2 of CDP870.

SEQ ID NO: 6 shows the amino acid sequence of CDRL3 of CDP870.

SEQ ID NO: 7 shows the nucleotide and predicted amino acid sequence of the light chain variable region CDP870.

SEQ ID NO: 8 shows the nucleotide and predicted amino acid sequence of the heavy chain variable region CDP870.

SEQ ID NO: 9 shows the amino acid sequence of a grafted anti-TNFα Fab CDP870 light chain.

SEQ ID NO: 10 shows the amino acid sequence of a grafted anti-TNFα Fab CDP870 heavy chain.

SEQ ID NO: 11 is the nucleotide sequence of his-tagged DsbC.

SEQ ID NO: 12 is the amino acid sequence of his-tagged DsbC.

SEQ ID NO: 13 is the sequence of the wild-type spr gene including the signal sequence which is the first 26 amino acid residues.

SEQ ID NO: 14 is the sequence of the wild-type spr gene without the signal sequence.

SEQ ID NO: 15 is the DNA sequence of a mutated knockout Tsp gene including the 6 nucleotides ATGAAT upstream of the start codon.

SEQ ID NO: 16 shows the oligonucleotide cassette encoding intergenic sequence 2 (IGS2) for *E. coli* Fab expression.

DETAILED DESCRIPTION OF THE PREFERRED EMBODIMENTS OF THE INVENTION

The present invention will now be described in more detail.

The terms "protein" and "polypeptide" are used interchangeably herein, unless the context indicates otherwise. "Peptide" is intended to refer to 10 or less amino acids.

The terms "polynucleotide" includes DNA, cDNA, RNA and mRNA.

As used herein, the term "comprising" in context of the present specification should be interpreted as "including".

The expressions "cell", "cell line", "cell culture" and "strain" are used interchangeably.

Host cell extract (extract therefrom) as employed herein is used to refer to part or all of the host cell contents i.e.
  material obtained from a partial or total cell lysis to extract some or all chemical matter from the cells, or
  material obtained from subjecting the cells to processing such that one or more of the proteins expressed from the cells are released into the liquid phase.

Chemical matter and material that form the contents of the host cell as employed herein refer to liquids, proteins, lipids, sugars, lipopolysaccharides, peptidoglycans, plasmid and chromosomal DNA's, RNA's, small molecules such as amino acids, metal ions, redox active molecules, tRNA's and fragments of all of the above from within the cell.

Methods for releasing one or more proteins from the cells include heat treatment and/or subjecting the cells non-lysing pressure and/or use of chemicals including: buffers, chelating agents, detergents, physical disruption and/or use sonic energy and/or use of mechanical shear.

Gram-negative cell sample as employed herein refers to a population of gram-negative cells, for example at least two gram-negative cells but more specifically a batch employed in a fermentation process, in particular a commercial fermentation process.

Purified recombinant antibody or binding fragment thereof as employed herein is intended to refer to a form of the antibody or fragment wherein there are less impurities and contaminates than in the corresponding unprocessed form. It is not necessarily intended to be an absolute term because the antibody or fragment may still require further purification steps.

In one embodiment a purified recombinant antibody or binding fragment thereof provided by the method according to the present invention is substantially pure.

Substantially pure as employed herein refers to the where the antibody or binding fragment thereof is great than 90% pure, for example 91, 92, 93, 94, 95, 96, 97, 98, 99 or 100% pure, in particular 95% pure or greater.

This invention described herein is based on the surprising and unexpected observation that after a host cell sample transformed with an expression vector encoding a recombinant protein molecule has been cultured a step of adjusting the pH to 5 or less may be used to precipitate recombinant disulphide isomerase and that this has a significant beneficial impact on the purification of the protein.

Step a) of the present invention requires the adjustment of the host cell sample or extract thereof to a pH of 5 or less, a pH of less than 5, a pH of 4.5 or less or a pH of 3 or less. In a preferred embodiment, the pH of the host cell sample or extract thereof is adjusted to a pH of 4.5 or less, more preferably a pH of approximately 4.5. The inventors have found that a pH of 4.5 is particularly advantageous to precipitate and allow separation of recombinant DsbC.

In one embodiment the pH of the host cell sample or extract thereof is not adjusted to a pH which is less than pH 3 or alternatively less than pH 3.5. Accordingly, the pH of the host cell sample or extract thereof is preferably adjusted to a pH of 3 to 4.9, a pH of 3.5 to 4.9, a pH of 3 to 4.5 or a pH of 3.5 to 4.5.

In one embodiment the pH of the host cell sample or extract thereof is adjusted to a pH of 3 or less, more preferably a pH of approximately 3. The inventors have found that a pH of 3 of less is advantageous to precipitate and allow separation of recombinant DsbC and also host cell dipeptide binding protein.

However, whilst pHs of 3 or less are suitable for precipitating the DsbC protein from the host cell or extract low pHs may alter the folded conformation of the antibody or binding fragment thereof and thus may not be optimal when all parameters of the process are considered.

Thus the optimal pH for precipitating the host cell proteins will depend on the specific antibody or antibody fragment expressed by the cell and in particular the stability of the same in the relevant pH range.

At least one disulfide isomerase, for example at least DsbC is precipitated employing the process. In one embodiment one or more other host cell proteins are also precipitated employing the process.

In step a) of the method of the present invention the host cell solution or extract thereof may be held at the lower pH, for example a pH of 5 or less for any suitable period of time before carrying out any further purification steps, such as centrifugation and/or filtration, and/or before a further pH adjustment typically to raise pH of the solution. Generally the host cell solution or extract thereof will be held for 24 hours or less, 12 hours or less, 6 hours or less, 5 hours or less, 2 hours or less, 1 hour or less, 30 minutes or less, 10 minutes or less or 7 minutes or less.

After employing the method of the invention the pH may, for example be raised to pH 6, 6.5 or 7 before the further i.e. subsequence processing such as further purification, for example purification employing anion exchange chromatography is performed.

Step a) of the method of the present invention may be performed at any suitable temperature, for example room temperature, such as 20-23° C. or reduced temperature such 1-10° C. Thus suitable temperature ranges for performing the method include at least 1 to 30° C.

The adjustment of the pH of the host cell sample or extract thereof may be performed using any suitable agent capable of changing the pH. Examples of suitable agents are glacial acetic acid, sodium hydroxide, sodium acetate or tris base, and combination thereof. The agent may be at any suitable concentration such as 30 or 60% (v/v) glacial acetic acid, 1M sodium hydroxide, 1M sodium acetate, and 2M or 3M tris base.

One or more of these agents are particularly advantageous for use in the method according to the present disclosure and, for example enabling precipitation and removal of the recombinant disulphide isomerase in the purification of a therapeutic protein because they are non-toxic.

Disulphide isomerase is an enzyme that catalyzes the formation and breakage of disulphide bonds between cysteine residues within proteins as they fold. Protein disulphide isomerase is released from the host cell upon extraction of the recombinant protein. The host cell used in the method of the present invention produces recombinant disulphide isomerase and, therefore, the recombinant disulphide isomerase constitutes a significant proportion of contaminating host cell protein. The present invention has provided a time and cost-saving means to remove the recombinant disulphide isomerase from the recombinant protein. The recombinant disulphide isomerase, such as DsbC, may comprise a histidine tag (his-tag) at the N- and/or C-terminus.

The histidine tag is advantageous because it allows effective monitoring to show that DsbC contamination has been removed from the antibody or binding fragment thereof. This is important because the presence of DsbC can be difficult to detect when using polyclonal sera raised against the cellular contents from wild type *E. coli* because standard polyclonal sera tend to be poorly reactive or non-reactive to DsbC, and so are unable to detect DsbC even when it is overexpressed at high levels. The presence of a detection tag such as poly-His ensures that the removal of abundantly overexpressed DsbC can be monitored/confirmed using sensitive immunodetection methods.

In a preferred embodiment, the recombinant disulphide isomerase is DsbC. DsbC is a prokaryotic protein found in the periplasm of *E. coli* which catalyzes the formation of disulphide bonds in *E. coli*. DsbC has an amino acid sequence length of 236 (including signal peptide) and a molecular weight of 25.6 KDa (UniProt No. P0AEG6). DsbC was first identified in 1994 (Missiakas et al. The *Escherichia coli* dsbC (xprA) gene encodes a periplasmic protein involved in disulfide bond formation, The EMBO Journal vol 13, no 8, p 2013-2020, 1994 and Shevchik et al. Characterization of DsbC, a periplasmic protein of *Erwinia*

*chrysanthemi* and *Escherichia coli* with disulfide isomerase activity, The EMBO Journal vol 13, no 8, p 2007-2012, 1994). The DsbC protein may comprise a histidine tag (his-tag) at the N- and/or C-terminus.

The predicted pI of DsbC is 5.7 and the predicted pI of his-tagged DsbC is 6.3. The pI of a protein can be predicted using a variety of commercially available and free to public softwares and on-line pI prediction facilities such as ExPASy ProtParam.

Figure 3:
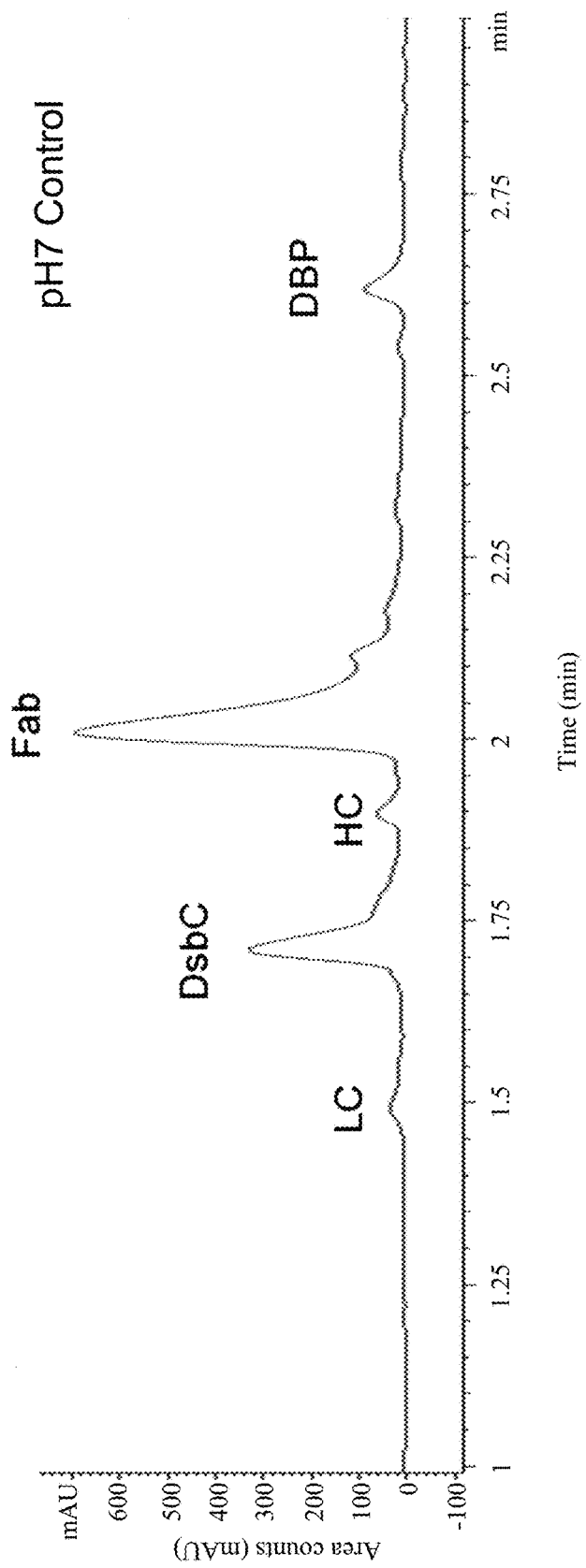
FIG. 3 shows the separate chromatograms of a reverse phase HPLC analysis at T=0 for host cell solutions after pH adjustment to pH 5, pH 4.5 or pH 3 compared to the control pH of 7.
Figure 3:
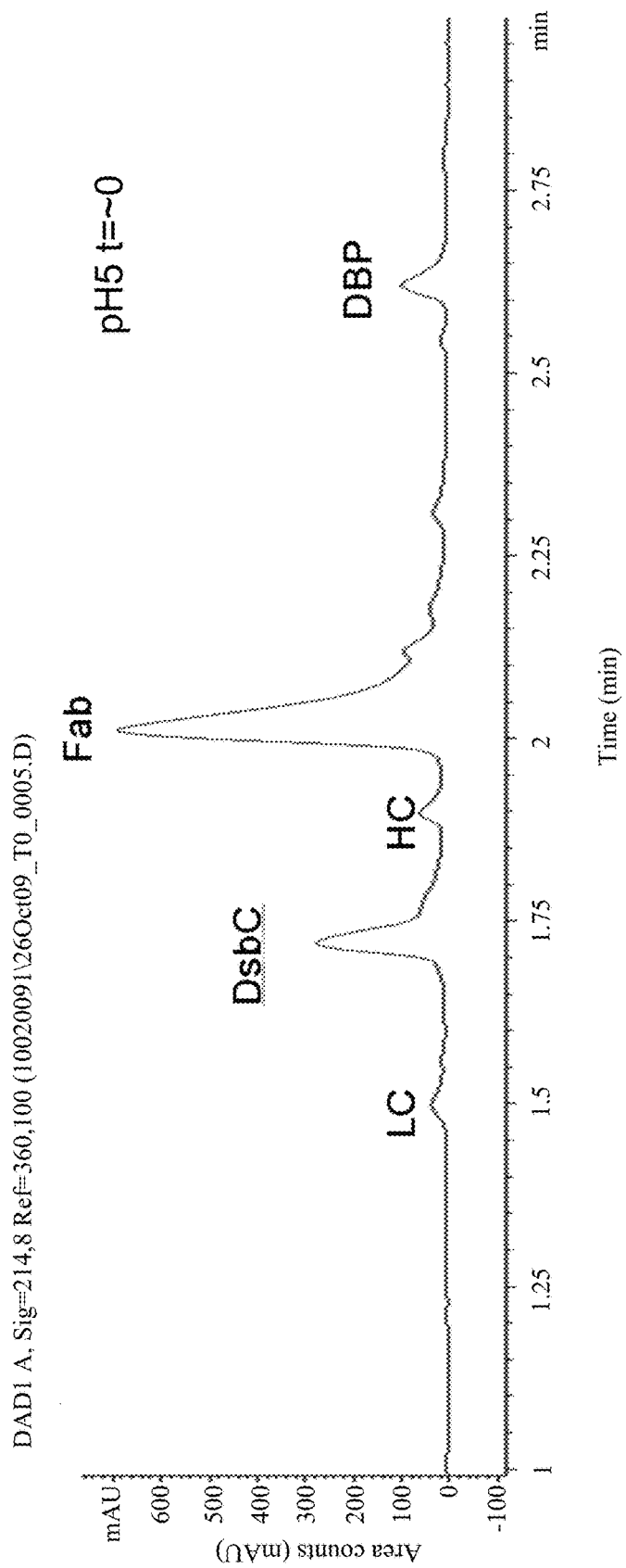
Figure 3:
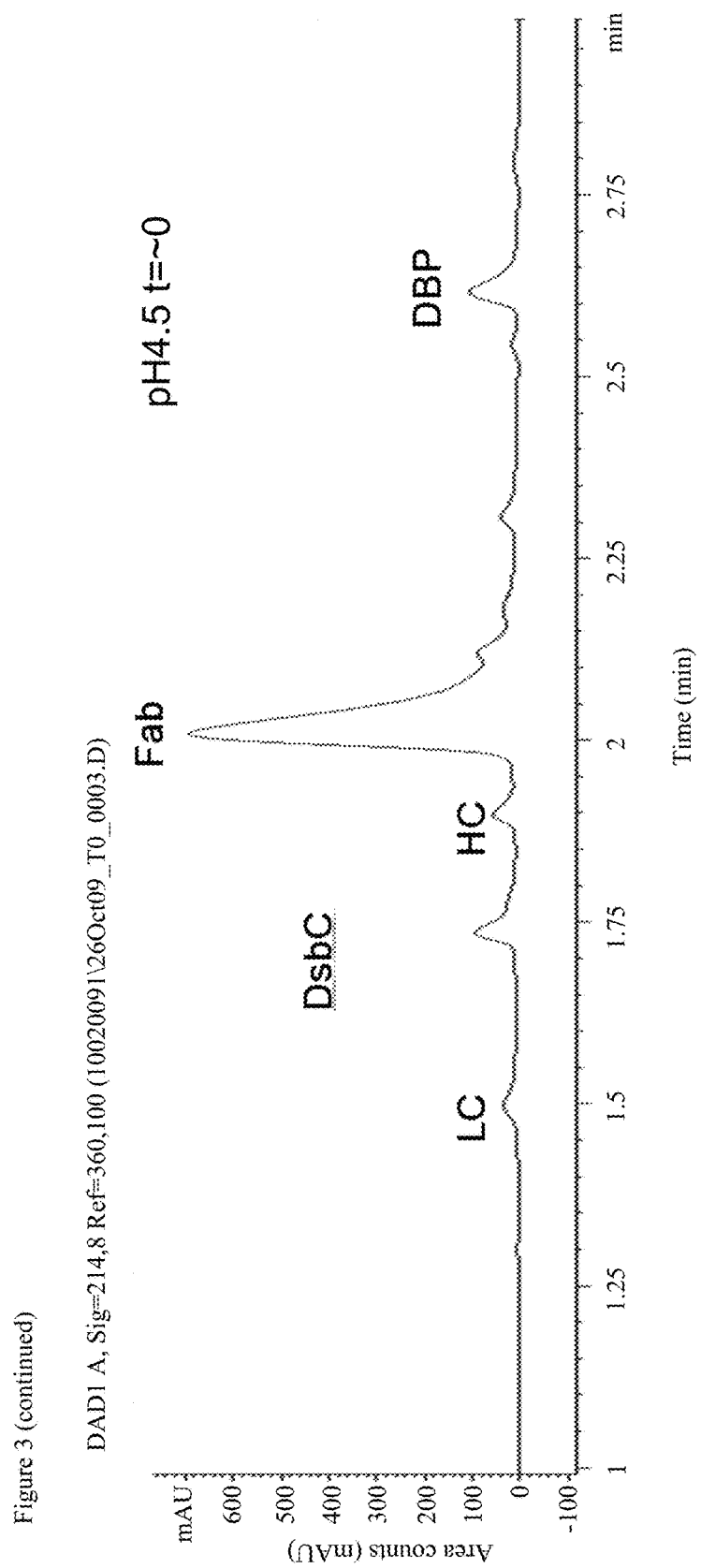
Figure 3:
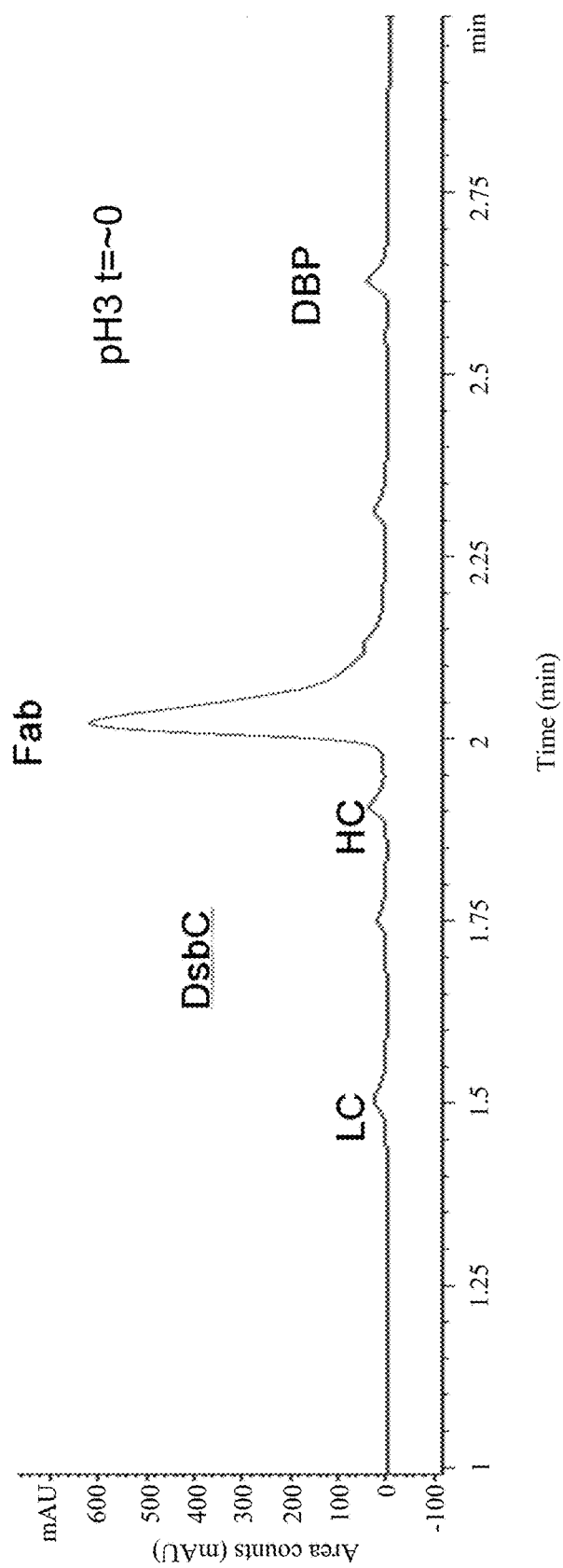

Proteins may be expected to precipitate if the pH of the solution passes through the pI of the protein. However, it can be seen from FIG. 4 that a solution of DsbC (his-tagged) free of host cell or host cell extract when adjusted to pH 3 does not precipitate because the quantity of DsbC is not reduced after the pH adjustment. Surprisingly, it has been found that DsbC does precipitate when a host cell sample or extract thereof comprising recombinant DsbC is subjected to a pH adjustment to less than pH 5 a significant amount of the DsbC is precipitated and can be separated from a recombinant protein of interest, as shown in FIG. 3. Accordingly, it is not possible to predict from the predicted pI of a protein, such as DsbC, what pH is required to allow precipitation from a host cell sample or extract thereof.

As used herein, a "recombinant polypeptide" refers to a protein that is constructed or produced using recombinant DNA technology. The polynucleotide sequence encoding disulphide isomerase may be identical to an endogenous sequence encoding disulphide isomerase found in bacterial cells. Alternatively, the recombinant polynucleotide sequence encoding the disulphide isomerase is a mutated version of the wild-type disulphide isomerase sequence, for example having a restriction site removed. In the embodiment wherein the disulphide isomerase is DsbC, the restriction site EcoRI may be removed and/or a sequence encoding a his-tag added. An example modified DsbC nucleotide sequence for use in the present invention is shown in SEQ ID NO: 11, which encodes the his-tagged DsbC amino acid sequence shown in SEQ ID NO: 12.

In one embodiment the mutant DsbC consists of a DsbC protein with a mutated active site represented by —CXXC— wherein XX is TF, GF, HH, NY, SF, MF, VH, SH, RF, FA, GA, MA, GI, AV, PS, QA, SV, PR, PP, AL, PL, FL, TR, LL, VL, QL, LQ.

Prior to step a) of the method of the present invention, the method may comprise culturing a host cell sample transformed with one or more expression vectors encoding a recombinant protein and a recombinant disulphide isomerase. The sample may be at any suitable scale from small-scale production of protein to large-scale manufacture of protein for commercial purposes.

In one embodiment, wherein the protein is an antibody, the recombinant antibodies produced from the host cell may be a mixture of functional and non-functional antibodies.

The host cell comprises a recombinant polynucleotide encoding a disulphide isomerase which may be present on a suitable expression vector transformed into the cell and/or integrated into the host cell's genome. Preferably the polynucleotide encoding the disulphide isomerase is in an expression vector in the cell thereby causing minimal disruption to the host cell's genome. The recombinant protein and the recombinant disulphide isomerase may be present on the same expression vector or on separate expression vectors.

The cells used in the present invention are gram-negative bacteria. Most preferably, the cells are *E. coli*. The cells are recombinant cells which have been genetically engineered. *E. coli* host cells are mutated strains capable of producing recombinant proteins. The recombinant *E. coli* host cells may be derived from any suitable *E. coli* strains include MC4100, TG1, TG2, DHB4, DH5α, DH1, BL21, K12, XL1Blue and JM109. One example is *E. coli* W3110 (ATCC 27,325) a commonly used host strain for recombinant protein fermentations. Examples also include modified *E. coli* strains, for example metabolic mutants and protease deficient strains.

The host cell is genetically engineered to produce recombinant disulphide isomerase. Host cells which produce recombinant disulphide isomerase are particularly advantageous because the presence of the recombinant disulphide isomerase may reduce cell lysis and may assist in the processing of the recombinant protein.

In a preferred embodiment the host cell comprises a polynucleotide sequence encoding recombinant DsbC, including his-tagged DsbC.

The host cell according to the present invention may comprise one or more further genetic modifications.

In one embodiment, the host cell may have reduced protease activity, wherein the cell comprises a mutated Tsp gene encoding a Tsp protein having reduced protease activity or is a knockout mutated Tsp gene.

For example, the host cell may have reduced Tsp protein activity compared to a wild-type cell. Tsp (also known as Prc) is a 60 kDa periplasmic protease. The first known substrate of Tsp was Penicillin-binding protein-3 (PBP3) (Determination of the cleavage site involved in C-terminal processing of penicillin-binding protein 3 of *Escherichia coli*; Nagasawa H, Sakagami Y, Suzuki A, Suzuki H, Hara H, Hirota Y. J Bacteriol. 1989 November; 171(11):5890-3 and Cloning, mapping and characterization of the *Escherichia coli* Tsp gene which is involved in C-terminal processing of penicillin-binding protein 3; Hara H, Yamamoto Y, Higashitani A, Suzuki H, Nishimura Y. J Bacteriol. 1991 August; 173 (15):4799-813) but it was later discovered that the Tsp was also able to cleave phage tail proteins and, therefore, it was renamed as Tail Specific Protease (Tsp) (Silber et al., Proc. Natl. Acad. Sci. USA, 89: 295-299 (1992)).

In this embodiment the cell has reduced Tsp protein activity compared to a wild-type cell. The expression "reduced Tsp protein activity compared to a wild-type cell" means that the Tsp activity of the cell is reduced compared to the Tsp activity of a wild-type cell. The cell may be modified by any suitable means to reduce the activity of Tsp. In one embodiment the reduced Tsp activity is from modification of the endogenous polynucleotide encoding Tsp and/or associated regulatory expression sequences. The modification may reduce or stop Tsp gene transcription and translation or may provide an expressed Tsp protein having reduced protease activity compared to the wild-type Tsp protein. In one embodiment an associated regulatory expression sequence is modified to reduce Tsp expression. For example, the promoter for the Tsp gene may be mutated to prevent expression of the gene. In a preferred embodiment the cell according to the present invention carries a mutated Tsp gene encoding a Tsp protein having reduced protease activity or a knockout mutated Tsp gene. Preferably the chromosomal Tsp gene is mutated.

The reduction of Tsp (prc) activity is desirable to reduce the proteolysis of proteins of interest. However, it was found that cells lacking protease prc show thermosensitive growth at low osmolarity. Hara et al isolated thermoresistant revertants containing extragenic suppressor (spr) mutations (Hara et al., Microbial Drug Resistance, 2: 63-72 (1996)). Spr is an 18 kDa membrane bound periplasmic protease and the substrates of spr are Tsp and peptidoglycans in the outer membrane involved in cell wall hydrolysis during cell division. The spr gene is designated as UniProtKB/Swiss-Prot P0AFV4 (SPR_ECOLI). Improved protease deficient strains comprising mutant spr gene have been described. Chen et al (Chen C, Snedecor B, Nishihara J C, Joly J C, McFarland N, Andersen D C, Battersby J E, Champion K M. Biotechnol Bioeng. 2004 March 5; 85(5):463-74) describes the construction of *E. coli* strains carrying different combinations of mutations in prc (Tsp) and another protease, DegP, created by amplifying the upstream and downstream regions of the gene and ligating these together on a vector comprising selection markers and a sprW174R mutation (High-level accumulation of a recombinant antibody fragment in the periplasm of *Escherichia coli* requires a triple-mutant (ΔDegP Δprc sprW174R) host strain.

The wild-type amino acid sequence of the spr protein is shown in SEQ ID NO:13 with the signal sequence at the N-terminus and in SEQ ID NO:14 without the signal sequence of 26 amino acids (according to UniProt Accession Number P0AFV4). The amino acid numbering of the spr protein sequence in the present invention includes the signal sequence. Accordingly, the amino acid 1 of the spr protein is the first amino acid (Met) shown in SEQ ID NO: 13.

In a further embodiment the cell comprises a mutated spr gene. The mutant spr gene encoding a spr protein may have a mutation at one or more amino acids selected from C94, S95, V98, Y115, D133, V135, H145, G147, H157 and W174. Preferably the mutant spr gene encodes a spr protein having a mutation at one or more amino acids selected from C94, S95, V98, Y115, D133, V135, H145, G147 and H157. Preferably, the mutant spr gene encodes a spr protein having a mutation at one or more amino acids selected from S95, V98, Y115, D133, V135 and G147. The spr mutations are capable of suppressing the growth phenotype of a cell comprising a mutated Tsp gene.

One or more of the amino acids C94, S95, V98, Y115, D133, V135, H145, G147, H157 and W174 may be mutated to any suitable amino acid which results in a spr protein capable of suppressing the phenotype of a cell comprising a mutated Tsp gene. For example, one or more of S95, V98, Y115, D133 and V135 may be mutated to a small amino acid such as Gly or Ala. In a preferred embodiment the spr protein comprises one or more of the following mutations: C94A, S95F, V98E, Y115F, D133A, V135D or G, H145A, G147C and H157A.

In a further embodiment the mutated spr gene encodes a spr protein having the mutation W174R. In an alternative embodiment the spr protein does not have the mutation W174R.

The designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid.

Accordingly, in a preferred embodiment the cell used in the present invention comprises a recombinant polynucleotide encoding DsbC and a mutated spr gene, as defined above.

In a further preferred embodiment the cell used in the present invention has reduced Tsp protein activity compared to a wild-type cell and comprises a recombinant polynucleotide encoding DsbC and a mutated spr gene, as defined above.

In one embodiment the host cell comprises a mutated DegP gene encoding a DegP protein having chaperone activity and reduced protease activity and/or a mutated ptr gene, wherein the mutated ptr gene encodes a Protease III protein having reduced protease activity or is a knockout mutated ptr gene and/or a mutated OmpT gene, wherein the mutated OmpT gene encodes an OmpT protein having reduced protease activity or is a knockout mutated OmpT gene.

In one embodiment the host cell expresses one or more proteins as follows:
one or more proteins capable of facilitating protein folding, such as FkpA, Skp, SurA, PPiA and PPiD; and/or
one or more protein capable of facilitating protein secretion or translocation, such as SecY, SecE, SecG, SecYEG, SecA, SecB, FtsY and Lep; and/or
one or more proteins capable of facilitating disulphide bond formation, such as DsbA, DsbB, DsbD, DsbG.
One of more of the above proteins may be integrated into the cell's genome and/or inserted in an expression vector.

In one embodiment the host cell does not comprise recombinant polynucleotide encoding one or more of the following proteins:
one or more proteins capable of facilitating protein folding, such as FkpA, Skp, SurA, PPiA and PPiD;
one or more protein capable of facilitating protein secretion or translocation, such as SecY, SecE, SecG, SecYEG, SecA, SecB, FtsY and Lep; and
one or more proteins capable of facilitating disulphide bond formation, such as DsbA, DsbB, DsbD, DsbG.

In one embodiment the cell used in the present invention has reduced Tsp protein activity compared to a wild-type cell and comprises a recombinant polynucleotide encoding DsbC and a mutated spr gene, as defined above comprises a recombinant polynucleotide encoding DsbC and a mutated spr gene, as defined above, and FkpA and/or Skp.

The recombinant protein produced using the methods of the present invention is typically expressed in either the periplasm of the *E. coli* host cell or in the host cell culture supernatant, depending on the nature of the protein and the scale of production. The methods for targeting proteins to these compartments are well known in the art, for a review see Makrides, Microbiological Reviews, 1996, 60, 512-538. Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the coexpression of bacteriocin release protein, the mitomycin-induced bacteriocin release protein along with the addition of glycine to the culture medium and the coexpression of the kil gene for membrane permeabilization. Most preferably, in the methods of the invention, the recombinant protein is expressed in the periplasm of the host *E. coli*.

Expression of the recombinant protein in the *E. coli* host cells may also be under the control of an inducible system, whereby the expression of the recombinant protein in *E. coli* is under the control of an inducible promoter. Many inducible promoters suitable for use in *E. coli* are well known in the art and, depending on the promoter, expression of the recombinant protein can be induced by varying factors such as temperature or the concentration of a particular substance in the growth medium (Baneyx, Current Opinion in Biotechnology, 1999, 10:411-421; Goldstein and Doi, 1995, Biotechnol. Annu. Rev, 105-128). Examples of inducible promoters include the *E. coli* lac, tac, and trc promoters which are inducible with lactose or the non-hydrolyzable lactose analog, isopropyl-β-D-1-thiogalactopyranoside (IPTG) and the phoA, trp and araBAD promoters, which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression; for example, where the inducer is lactose there may be a delay before induction of protein expression occurs while any pre-existing carbon source is utilized before lactose.

E. coli host cell cultures (fermentations) may be cultured in any medium that will support the growth of E. coli and expression of the recombinant protein. The medium may be any chemically defined medium, such as those provided in Pirt S. J. (1975) Principles of Microbe and Cell Cultivation, Blackwell Scientific Publications, with modifications where appropriate to control growth rate as described herein. An example of a suitable medium is 'SM6E' as described by Humphreys et al., 2002, Protein Expression and Purification, 26:309-320.

Culturing of the E. coli host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 10,000 or 12,000 liters. Smaller scale fermenters may also be used with a capacity of between 0.5 and 1,000 liters.

Fermentation of E. coli may be performed in any suitable system, for example continuous, batch or fed-batch mode (Thiry & Cingolani, 2002, Trends in Biotechnology, 20:103-105) depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the E. coli host cells and to allow higher cell densities to be reached (Lee, 1996, Tibtech, 14:98-105).

If desired, the host cells may be subject to collection from the fermentation medium, e.g. host cells may be collected from the sample by centrifugation, filtration or by concentration. In particular, the methods of the invention are suitable for the large-scale industrial manufacture of antibodies of therapeutic quality.

In one embodiment the method according to the present invention comprises a step of centrifugation after the step of culturing, followed by suspension of the cells by addition of the extraction buffer.

Following the step of culturing, the method may comprise a step of extraction to release the recombinant protein from the host cell. The extraction may be performed by any suitable method such as cell lysis by mechanical or pressure treatment, freeze-thaw treatment, osmotic shock, extraction agents or heat treatment. Such extraction methods are well-known in the art.

In a preferred embodiment an extraction buffer is added to the sample and the sample is then subjected to a heat treatment step. The heat treatment step is preferably as described in detail in U.S. Pat. No. 5,665,866 (the contents of which are incorporated herein by reference). The heat treatment step makes it possible to obtain a sample of soluble, correctly folded and assembled antibody by facilitating the removal of other antibody-related material. Antibody which is "correctly folded and assembled" is shown by the presence of a single band corresponding to the expected molecular weight for assembled heavy and light chains on non-reducing SDS PAGE. Other antibody related material will typically be free heavy and light chain or part thereof, partially degraded fragments of correctly folded and assembled antibody.

The heat treatment step is performed by subjecting the sample to a desired elevated temperature. Most preferably, heat treatment step is performed within the range of 30° C. to 70° C., The temperature can be selected as desired and may depend on the stability of the protein for purification. In another embodiment, the temperature is within the range 40° C. to 65° C., or preferably within the range 40° C. to 60° C., more preferably within the range 45° C. to 60° C., even more preferably within the range 50° C. to 60° C. and most preferably at 55° C. to 60° C., 58° C. to 60° C. or 59° C. Thus, the minimum temperatures are 30° C., 35° C. or 40° C. and the maximum temperatures 60° C., 65° C. or 70° C.

The heat treatment step is preferably carried out for a prolonged period of time. The length of heat treatment is preferably between 1 and 24 hours, more preferably between 4 and 18 hours, even more preferably between 6 and 16 hours and most preferably between 10 and 14 hours or between 10 and 12 hours, for example 12 hours. Thus, the minimum time for heat treatment is 1, 2 or 3 hours and the maximum is 20, 22 or 24 hours.

In a particular embodiment, the heat treatment is performed at 50° C. to 60° C. for 10 to 16 hours, and more preferably at 59° C. for 10 to 12 hours. One skilled in the art will understand that temperatures and time can be selected as suits the sample in question and the characteristics of the protein being produced.

Following the step of extraction the sample may be subjected to a step of centrifugation and/or filtration prior to the step of adjusting the pH.

The sample which is subjected to step a) of the present invention is a host cell sample or extract thereof. Accordingly, step a) may, for example be carried out on:
- a solution comprising the population of host cells expressing the recombinant protein and recombinant disulphide isomerase;
- the supernatant of the population host cells expressing the recombinant protein and recombinant disulphide isomerase following centrifugation and/or filtration to remove the host cells;
- the extract of the population of host cells expressing the recombinant protein and recombinant disulphide isomerase following a step of extraction, such as heat treatment; or
- the extract of the population of host cells expressing the recombinant protein and recombinant disulphide isomerase following a step of extraction, such as heat treatment, and one or more subsequent steps of centrifugation and/or filtration.

Prior to step a), the host cell solution or extract thereof is at a suitable pH, typically the pH of the host cell solution or extract thereof is pH 5 to 10, preferably pH 6 to 8 or approximately pH 7. The pH of the host cell solution or extract thereof prior to step a) may depend on the pI of the recombinant protein of interest. Proteins may have a tendency to precipitate if the pH is adjusted to or through the pI of the protein. Therefore, it is preferable that the pH of the solution prior to the pH adjustment step is lower than the pI of the recombinant protein to ensure that the pH adjustment step does not bring the pH of the solution to or through the pI of the recombinant protein. For example, if the pI of the recombinant protein is around 8, the pH of the solution is preferably less than pH 8 in order to minimize precipitation of the recombinant protein. The step of lowering the pH to less than pH 5 will also preferably avoid the pI of the recombinant protein.

The pI of a protein will depend upon the ionic strength of the solution it is in. Accordingly, the calculated pI of a protein in water or very low ionic strength buffer may be different to the pI of a protein in a host cell sample or extract thereof comprising buffer and HCPs. The pI of a protein may be 1, 1.5 or 2 pH units lower than the measured pI of the protein in water or very low ionic strength buffer. Therefore, the pH of the host cell solution or extract thereof is preferably kept at a pH of 1, 1.5 or 2 pH units below the pI of the recombinant protein of interest measured in water or very low ionic strength buffer.

In step b) of the method according to the present invention, the precipitated recombinant disulphide isomerase is separated from the recombinant protein to produce a recombinant protein sample. Step b) typically comprises centrifugation and/or filtration in order to separate the precipitated recombinant disulphide isomerase.

The resulting recombinant protein sample has a reduced quantity of recombinant disulphide isomerase compared to the quantity of recombinant disulphide isomerase prior to step a). Preferably the recombinant protein sample after step b) is substantially free of recombinant disulphide isomerase. However, it is possible that some recombinant disulphide isomerase will remain in the sample, which may be removed by later purification steps. The skilled person can determine if recombinant disulphide isomerase is still present in the recombinant protein sample using methods well known in the art. For example, an ELISA analysis may be used to detect the recombinant disulphide isomerase, such as DsbC. An antibody specific for the recombinant disulphide isomerase, such as DsbC, may be used or if the recombinant disulphide isomerase is his-tagged, such as DsbC-his-tag, an anti-His-tag antibody may be used for detection of the recombinant disulphide isomerase.

Substantially free of as employed herein is intended to refer to containing 5% w/w or less, such as 4, 3, 2, 1 or 0.5% w/w or less.

In one embodiment, where the pH of the host cell sample or extract thereof is adjusted to a pH of 3 or less (such as pH 3), the host cell protein dipeptide binding protein (also referred to as "DBP") is precipitated and separated from the recombinant protein in step b). In this embodiment the resulting recombinant protein sample also has reduced quantity of host cell dipeptide binding protein (DBP). Preferably the resulting recombinant protein sample is substantially free of DBP.

Preferably the resulting recombinant protein sample also has reduced quantity of other host cell proteins which may also precipitate during step a). Preferably the resulting recombinant protein sample is substantially free of other host cell proteins.

The yield of the recombinant protein of interest following steps a) and b) of the present invention is typically 75% or more, 80% or more, 85% or more or 90% or more.

After step b), the pH of the recombinant protein sample may be adjusted to a suitable pH for either storing the recombinant protein or for performing a downstream purification step, such as chromatography. As discussed previously, the pH of the solution can be adjusted to minimize precipitation of the recombinant protein of interest by ensuring that the pH is not at the pI of the recombinant protein. Preferably the pH of the recombinant protein sample is adjusted to a pH of 5 to 7, more preferably a pH of 5 to 6. The exact pH required will depend upon the properties of the recombinant protein, including the pI of the protein, and which downstream purification steps are to be carried out. Any suitable agent may be used to adjust the pH of the recombinant protein sample, such as a base selected from NaOH, Na Acetate or Tris base.

Alternatively, the method does not comprise a step of pH adjustment after step b). In this embodiment, the pH of the recombinant protein sample may be suitable for storage of the recombinant protein and/or for one or more subsequent downstream purification steps. In one embodiment, in step a) the pH of the host cell sample or extract thereof is adjusted to a pH of 4.5, step b) comprises centrifugation and filtration and the resulting recombinant protein solution after step b) is then subjected to a cation exchange chromatography step at pH 4.5.

Alternatively a chromatography step may be performed at higher pH, for example pH or above, such as 5 to 8, in particular 6 or 7.

Following step b), the recombinant protein sample may be subjected to one or more further purification steps in order to remove contaminants and/or undesired protein fragments such as antibody fragments. Typically the recombinant protein sample is subjected to one or more steps of chromatography, wherein each step of chromatography may be followed by a step of filtration, such as microfiltration, diafiltration or ultrafiltration. The one or more steps of chromatograph may be affinity or non-affinity chromatography steps. In one embodiment the chromatograph is a non-affinity chromatography step such as cation or anion ion-exchange chromatography.

In one embodiment, in step a) the pH of the host cell sample or extract thereof is adjusted to a pH of 4.5, step b) comprises centrifugation and filtration and the resulting recombinant protein solution after step b) is then subjected to a cation exchange chromatography step at pH 4.5.

The method of the present invention is particularly advantageous when non-affinity chromatography steps are used in the downstream purification. This is because a large quantity of host cell proteins, including recombinant disulphide isomerase, may bind to the chromatography columns if they have not been previously separated. Accordingly, the capacity of the chromatography column to bind the desired recombinant protein is reduced. The separation of host cell proteins, including recombinant disulphide isomerase increases the capacity of subsequent non-affinity chromatography columns which provides a faster and cheaper means for purification of the recombinant protein.

During step a) of the present invention, the recombinant protein may partially unfold whilst the solution is held at the pH of 5 or less. However, partial unfolding of the protein is reversible and following the separation of the precipitated disulphide isomerase, the pH of the protein solution may be adjusted to a pH above 5, preferably a pH of 5 to 7, or pH of 5 to 6, and the protein may then adopt it's original folded conformation. Thus overall the low pH holding step provides relatively gentle conditions for removing impurities, with minimal long term consequence. The recombinant protein sample provided by the method of the present invention comprises a significant proportion of functional protein.

The recombinant protein of interest expressed by the host cells, preferably has a pI of 6 or higher, more preferably pI of 7 or higher. As discussed previously, if the protein has a pI of 6 or higher is it easier to minimize precipitation of the protein by keeping the pH of the sample below the pI of the protein, preferably 1, 1.5 or 2 pH units below the pI of the protein in water or very low ionic strength buffer, and the step of adjusting the pH of the sample to pH 5 or less does not adjust the pH of the solution to the pI of the protein.

The recombinant protein of interest is preferably a recombinant antibody. The recombinant antibody preferably has a pI of 6 to 10, 7 to 10, 6 to 9, 7 to 9, 8 to 9, 6, 7, 8 or 9. The pH of the sample is preferably kept below the pI of the recombinant antibody, more preferably 1, 1.5 or 2 pH units below the pI of the recombinant antibody, before, during and after step a) in order to ensure minimal precipitation of the antibody.

In a preferred embodiment, the recombinant antibody has a pI of 7-9 and the pH of the sample is adjusted to pH 3 to 4.5, more preferably pH 4.5, in step a).

A specific example of a recombinant antibody is an anti-TNF Fab' CDP870, as described herein and in WO01/094585, which has a pI of 8.

In one embodiment the recombinant antibody or binding fragment thereof is anti-TNF Fab' CDP870.

As used herein, 'functional antibody' includes antibody molecules that retain the ability to specifically recognise or bind to the antigen against which they were raised (cognate antigen) i.e. the antigen to which it is specific. The production of a functional antibody is shown by the presence of a single band on non-reducing SDS-PAGE corresponding to the expected molecular weight of the antibody, or by direct binding assay using BIAcore or other methods known to the person skilled in the art, for example but not limited to, ELISA. Non-functional antibodies include fragments which do not recognise their cognate antigen, and include incorrectly-folded or incorrectly-assembled antibodies, free heavy and light chains, and fragments thereof, including partially degraded fragments of antibodies which do not recognise or bind to their cognate antigen.

A binding fragment of an antibody is a fragment that is able to bind the antigen to which the antibody is specific.

In a preferred example, the recombinant antibody molecule is at least part of an antibody light chain and at least part of an antibody heavy chain, such that at least some of the expressed light and heavy chain antibody molecules are able to combine to form functional antibody.

As used herein, 'antibodies' include antibodies having full length heavy and light chains; functionally active fragments, binding fragments, derivatives or analogues thereof and may be, but are not limited to VH, VL, VHH, Fab, modified Fab, an altered hinge Fab, Fab', F(ab')$_2$ or Fv fragment; a light chain or heavy chain monomer or dimer; a single chain antibody, e.g. a single chain Fv in which the heavy and light chain variable domains are joined by a peptide linker, Fab-Fv, or a dual specificity antibody, such as a Fab-dAb, as described in PCT/GB2008/003331.

The antibodies may be polyclonal, monoclonal, bi-, tri- or tetra-valent antibodies, humanized or chimeric antibodies. These antibodies and their fragments may be naturally occurring, humanized, chimeric or CDR grafted antibodies and standard molecular biology techniques may be used to modify, add or delete amino acids or domains as desired. Humanized antibodies are antibody molecules from non-human species having one or more complementarity determining regions (CDRs) from the non-human species and a framework region from a human immunoglobulin molecule (see, for example, U.S. Pat. No. 5,585,089). The antibody molecules purified using the methods of the invention can be of any class (e.g. IgG, IgE, IgM, IgD and IgA) or subclass of immunoglobulin molecule.

The methods for creating these antibody molecules are well known in the art (see for example, Shrader et al., WO 92/02551; Ward et al., 1989, Nature, 341:544; Orlandi et al., 1989, Proc. Natl. Acad. Sci. USA, 86:3833; Riechmann et al., 1988, Nature, 322:323; Bird et al, 1988, Science, 242: 423; Queen et al., U.S. Pat. No. 5,585,089; Adair, WO91/09967; Mountain and Adair, 1992, Biotechnol. Genet. Eng. Rev, 10:1-142; Verma et al., 1998, Journal of Immunological Methods, 216:165-181).

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Bi-, tri- and tetra-valent antibodies may comprise multiple specificities or may be monospecific (see for example WO 92/22853).

Antibody sequences may also be generated using single lymphocyte antibody methods based on the molecular cloning and expression of immunoglobulin variable region cDNAs generated from single lymphocytes that were selected for the production of specific antibodies such as described by Babcook, J. et al., 1996, Proc. Natl. Acad. Sci. USA 93(15):7843-7848 and in WO 92/02551. The latter methods rely on the isolation of individual antibody producing cells which are then clonally expanded followed by screening for those clones which are producing an antibody which recognises its cognate antigen, and, if desired, the subsequent identification of the sequence of their variable heavy ($V_H$) and light ($V_L$) chain genes. Alternatively, the cells producing antibody that recognises its cognate antigen may be cultured together followed by screening.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD40L, CD45, CDW52, CD69, CD134 (OX40), ICOS, BCMP7, CD137, CD27L, CDCP1, CSF1 or CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, PD-1, DC-SIGN, TL1A, IL-7 receptor A and where appropriate, receptors thereof.

Soluble antigens include interleukins such as IL-1, IL-2, IL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α and referred to herein as TNF or TNFα), tumor necrosis factor-β, colony stimulating factors such as G-CSF or GM-CSF, and platelet derived growth factors such as PDGF-α, and PDGF-β, WISP-1 and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody may be used to functionally alter the activity of the antigen of interest. For example, the antibody may neutralize, antagonize or agonise the activity of said antigen, directly or indirectly.

In a preferred embodiment the antibody is an anti-TNF antibody, more preferably an anti-TNF Fab' CDP870, as described in WO01/094585 (the contents of which are incorporated herein by reference).

In one embodiment the antibody having specificity for human TNFα, comprises a heavy chain wherein the variable domain comprises a CDR having the sequence shown in SEQ ID NO:1 for CDRH1, the sequence shown in SEQ ID NO:2 for CDRH2 or the sequence shown in SEQ ID NO:3 for CDRH3.

In one embodiment the antibody comprises a light chain wherein the variable domain comprises a CDR having the sequence shown in SEQ ID NO:4 for CDRL1, the sequence shown in SEQ ID NO:5 for CDRL2 or the sequence shown in SEQ ID NO:6 for CDRL3.

In one embodiment the antibody comprises a heavy chain wherein the variable domain comprises a CDR having the sequence shown in SEQ ID NO:1 for CDRH1, the sequence shown in SEQ ID NO:2 for CDRH2 or the sequence shown in SEQ ID NO:3 for CDRH3 and a light chain wherein the variable domain comprises a CDR having the sequence shown in SEQ ID NO:4 for CDRL1, the sequence shown in SEQ ID NO:5 for CDRL2 or the sequence shown in SEQ ID NO:6 for CDRL3.

In one embodiment the antibody comprises SEQ ID NO:1 for CDRH1, SEQ ID NO: 2 for CDRH2, SEQ ID NO:3 for CDRH3, SEQ ID NO:4 for CDRL1, SEQ ID NO:5 for CDRL2 and SEQ ID NO:6 for CDRL3.

The antibody is preferably a CDR-grafted antibody molecule and typically the variable domain comprises human acceptor framework regions and non-human donor CDRs.

Preferably, the antibody comprises the light chain variable domain CDP870 (SEQ ID NO:7) and the heavy chain variable domain CDP870 (SEQ ID NO:8).

It is preferred that the antibody is a modified Fab fragment wherein the modification is the addition to the C-terminal end of its heavy chain one or more amino acids to allow the attachment of an effector or reporter molecule. Preferably, the additional amino acids form a modified hinge region containing one or two cysteine residue to which the effector or reporter molecule may be attached. Such a modified Fab fragment preferably has a heavy chain comprising or consisting of the sequence given as SEQ ID NO:10 and the light chain comprising or consisting of the sequence given as SEQ ID NO:9.

The host cell used in the present invention comprises DNA sequence encoding the antibody. Preferably, the DNA sequence encodes the heavy and the light chain of the antibody.

In one preferred embodiment, the DNA sequence encodes a light chain and comprises the sequence shown in SEQ ID NO:7 or SEQ ID NO:9 (CDP870) or a degenerate equivalent thereof.

In an alternatively preferred embodiment, the DNA sequence encodes a heavy chain and comprises the sequence shown in SEQ ID NO:8 or SEQ ID NO:10 (CDP870) or a degenerate equivalent thereof.

The DNA sequence of the may comprise synthetic DNA, for instance produced by chemical processing, cDNA, genomic DNA or any combination thereof.

The constant region domains of the antibody, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking TNFα activity.

Methods for the expression of recombinant proteins are well known in the art. Suitable examples of host cells for the expression of recombinant antibody molecules include bacteria such as gram positive or gram negative bacteria, e.g. *E. coli*, or yeast cells, e.g. *S. cerevisiae*, or mammalian cells, e.g. CHO cells and myeloma or hybridoma cell lines, e.g. NSO cells. Most preferably, in the methods of the invention, a recombinant antibody is produced in bacteria, e.g. *E. coli* (see Verma et al., 1988, J. Immunol. Methods 216:165-181; Simmons et al., 2002, J. Immunol. Methods 263:133-147).

After expression, the antibody may be further processed, for example by conjugation to another entity such as an effector molecule. Accordingly, the method according to the present invention may comprise a further step of attaching an effector molecule to the antibody.

The term effector molecule as used herein includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. Effector molecular may be attached to the antibody or fragment thereof by any suitable method, for example an antibody fragment may be modified to attach at least one effector molecule as described in WO05/003171 or WO05/003170 (the contents of which are incorporated herein by reference). WO05/003171 or WO05/003170 also describe suitable effector molecules.

The antibody may have a macrocycle, for chelating a heavy metal atom, or a toxin, such as ricin, attached to it by a covalent bridging structure. Alternatively, procedures of recombinant DNA technology may be used to produce an antibody molecule in which the Fc fragment (CH2, CH3 and hinge domains), the CH2 and CH3 domains or the CH3 domain of a complete immunoglobulin molecule has (have) been replaced by, or has attached thereto by peptide linkage, a functional non-immunoglobulin protein, such as an enzyme or toxin molecule. In the embodiment wherein the antibody is a modified Fab fragment having at the C-terminal end of its heavy chain one or more amino acids to allow attachment of an effector or reporter molecule, the additional amino acids preferably form a modified hinge region containing one or two cysteine residues to which the effector or reporter molecule may be attached.

A preferred effector group is a polymer molecule, which may be attached to the modified Fab fragment to increase its half-life in vivo.

The polymer molecule may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof. Particular naturally occurring polymers include lactose, amylose, dextran, glycogen or derivatives thereof. "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50,000 Da, preferably from 5000 to 40,000 Da and more preferably from 25,000 to 40,000 Da. The polymer size may in particular be selected on the basis of the intended use of the product. Thus, for example, where the product is intended to leave the circulation and penetrate tissue, for example for use in the treatment of a tumour, it may be advantageous to use a small molecular weight polymer, for example with a molecular weight of around 5,000 Da. For applications where the product remains in the circulation, it may be advantageous to use a higher molecular weight polymer, for example having a molecular weight in the range from 25,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 25,000 Da to about 40,000 Da.

Each polymer molecule attached to the modified antibody fragment may be covalently linked to the sulphur atom of a cysteine residue located in the fragment. The covalent linkage will generally be a disulphide bond or, in particular, a sulphur-carbon bond.

Where desired, the antibody fragment may have one or more effector or reporter molecules attached to it. The effector or reporter molecules may be attached to the antibody fragment through any available amino acid side-chain or terminal amino acid functional group located in the fragment, for example any free amino, imino, hydroxyl or carboxyl group. One or more effector or reporter molecules may be attached to an amino acid at or towards the C-terminal end of the heavy chain and/or the light chain of the antibody.

An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Shearwater Polymers Inc., Huntsville, Ala., USA) or may be prepared from commercially available starting materials using conventional chemical procedures.

As regards attaching poly(ethyleneglycol) (PEG) moieties, reference is made to "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York.

Where it is desired to obtain an antibody fragment linked to an effector or reporter molecule, this may be prepared by standard chemical or recombinant DNA procedures in which the antibody fragment is linked either directly or via a coupling agent to the effector or reporter molecule either before or after reaction with the activated polymer as appropriate. Particular chemical procedures include, for example, those described in WO 93/62331, WO 92/22583, WO 90,195 and WO 89/1476. Alternatively, where the effector or reporter molecule is a protein or polypeptide the linkage may be achieved using recombinant DNA procedures, for example as described in WO 86/01533 and EP-A-0392745.

Figure 2:
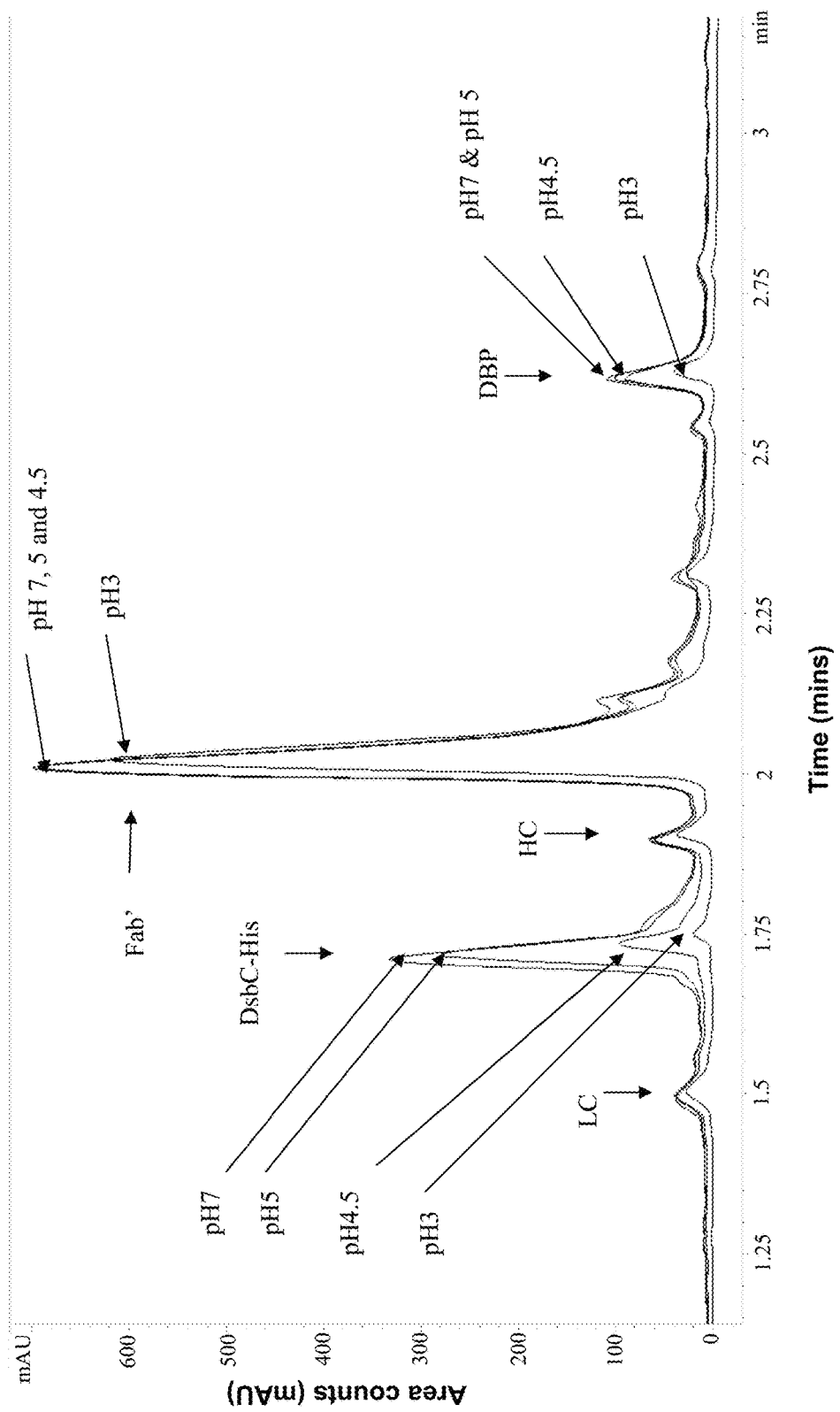
FIG. 2 shows the chromatogram of a reverse phase HPLC analysis at Time (T)=0 for host cell solutions after pH adjustment to pH 5, pH 4.5 or pH 3 compared to the control pH of 7.
Figure 9:
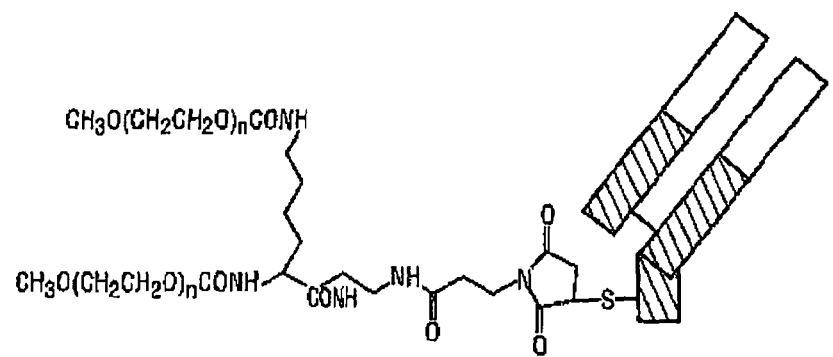
FIG. 9 shows the structure of a compound called CDP870 comprising a modified anti-TNF Fab' fragment covalently linked via a cysteine residue to a lysyl-maleimide linker wherein each amino group on the lysyl residue has covalently attached to it a methoxy PEG residue wherein n is about 420.

Preferably, the modified Fab fragment provided by the method of the present invention is PEGylated (i.e. has PEG (poly(ethyleneglycol)) covalently attached thereto) according to the method disclosed in EP-A-0948544. Preferably the antibody is a PEGylated modified Fab fragment as shown in FIG. 9. As shown in FIG. 2, the modified Fab fragment has attached to one of the cysteine residues at the C-terminal end of the modified hinge region of the heavy chain a lysyl-maleimide-derived group wherein each of the two amino groups of the lysyl residue has covalently linked to it a methoxypoly(ethyleneglycol) residue having a molecular weight of about 20,000 Da, such that the total average molecular weight of the methoxypoly(ethyleneglycol) residues is about 40,000 Da, more preferably the lysyl-maleimide-derived group is [1-[[[2-[[3-(2,5-dioxo-1-pyrrolidinyl)-1-oxopropyl]amino]ethyl]amino]-carbonyl]-1,5-pentanediyl]bis (iminocarbonyl). A lysine residue is covalently linked to the maleimide group. To each of the amine groups on the lysine residue is attached a methoxypoly(ethyleneglycol) polymer having a molecular weight of approximately 20,000 Da. The total molecular weight of the entire effector molecule is therefore approximately 40,000 Da.

Accordingly, the method according to the present invention preferably comprises attaching to one of the cysteine residues at the C-terminal end of the heavy chain a lysyl-maleimide group wherein each amino group of the lysyl residue has covalently linked to it a methoxypoly(ethyleneglycol) residue having a molecular weight of about 20,000 Da.

Preferably, in the compound shown in FIG. 9, the heavy chain of the antibody part has the sequence given as SEQ ID NO:10 and the light chain has the sequence given in SEQ ID NO:9. This compound is referred to herein as CDP870.

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

The present disclosure explicitly discloses embodiment comprising certain combinations of integers. The present disclosure also extends to embodiments consisting or consisting essentially of the said combinations of integers.

Preferences and/or embodiments may be combined as technically feasible.

The invention will now be described with reference to the following examples, which are merely illustrative and should not in any way be construed as limiting the scope of the present invention.

EXAMPLES

Example 1: Generation of Host Cell Line Expressing Recombinant DsbC and Recombinant Antibody For all experiments the *E. coli* cell line W3110 was used as the parental wild-type cell line. Cell lines were created carrying the following mutations:
 a. a mutated Tsp gene;
 b. a mutated Tsp gene and carrying recombinant DsbC;
 c. a mutated Tsp gene and a mutated spr gene;
 d. a mutated Tsp gene and a mutated spr gene and carrying recombinant DsbC.

Generation of Cell Line Carrying Mutated Tsp Gene MXE001 (ΔTsp)

The MXE001 strain was generated as follows:

The Tsp cassette was moved as Sal I, Not I restriction fragments into similarly restricted pKO3 plasmids. The pKO3 plasmid uses the temperature sensitive mutant of the pSC101 origin of replication (RepA) along with a chloramphenicol marker to force and select for chromosomal integration events. The sacB gene which encodes for levansucrase is lethal to *E. coli* grown on sucrose and hence (along with the chloramphenicol marker and pSC101 origin) is used to force and select for de-integration and plasmid curing events. This methodology had been described previously (Hamilton et al., 1989, *Journal of Bacteriology*, 171, 4617-4622 and Blomfield et al., 1991, *Molecular Microbiology*, 5, 1447-1457). The pKO3 system removes all selective markers from the host genome except for the inserted gene.

The following plasmids were constructed.

pMXE191 comprising the knockout mutated Tsp gene as shown in the SEQ ID NO: 15 comprising EcoR I and Ase I restriction markers.

The plasmid was then transformed into electro-competent competent *E. coli* W3110 cells prepared using the method found in Miller, E. M. and Nickoloff, J. A., "*Escherichia coli* electrotransformation," in Methods in Molecular Biology, vol. 47, Nickoloff, J. A. (ed.), Humana Press, Totowa, N.J., 105 (1995).

Day 1 40 μl of *E. coli* cells were mixed with (10 pg) 1 μl of pKO3 DNA in a chilled BioRad 0.2 cm electroporation cuvette before electroporation at 2500V, 25 μF and 200Ω. 1000 μl of 2×PY was added immediately, the cells recovered by shaking at 250 rpm in an incubator at 30° C. for 1 hour. Cells were serially 1/10 diluted in 2×PY before 100 μl aliquots were plated out onto 2×PY agar plates containing chloramphenicol at 20 μg/ml prewarmed at 30° C. and 43° C. Plates were incubated overnight at 30° C. and 43° C.

Day 2 The number of colonies grown at 30° C. gave an estimate of the efficiency of electroporation whilst colonies that survive growth at 43° C. represent potential integration events. Single colonies from the 43° C. plate were picked and resuspended in 10 ml of 2×PY. 100 μl of this was plated out onto 2×PY agar plates containing 5% (w/v) sucrose pre-warmed to 30° C. to generate single colonies. Plates were incubated overnight at 30° C.

Day 3 Colonies here represent potential simultaneous de-integration and plasmid curing events. If the de-integration and curing events happened early on in the growth, then the bulk of the colony mass will be clonal. Single colonies were picked and replica plated onto 2×PY agar that contained either chloramphenicol at 20 μg/ml or 5% (w/v) sucrose. Plates were incubated overnight at 30° C.

Day 4 Colonies that both grow on sucrose and die on chloramphenicol represent potential chromosomal replacement and plasmid curing events. These were picked and screened by PCR with a mutation specific oligonucleotide. Colonies that generated a positive PCR band of the correct size were struck out to produce single colonies on 2×PY agar containing 5% (w/v) sucrose and the plates were incubated overnight at 30° C.

Day 5 Single colonies of PCR positive, chloramphenicol sensitive and sucrose resistant *E. coli* were used to make glycerol stocks, chemically competent cells and act as PCR templates for a PCR reaction with 5' and 3' flanking oligos to generate PCR product for direct DNA sequencing using Taq polymerase.

Cell strain MXE001 was tested to confirm successful modification of genomic DNA carrying the mutated Tsp gene by PCR amplification of the region of the Tsp gene comprising a non-naturally occurring Ase I restriction site using oligonucleotides primers. The amplified regions of the DNA were then analyzed by gel electrophoresis before and after incubation with Ase I restriction enzyme to confirm the presence of the non-naturally occurring Ase I restriction site in the mutated genes.

The lysates were prepared by heating a single colony of cells for 10 minutes at 95° C. in 20 ul of 1×PCR buffer. The mixture was allowed to cool to room temperature then centrifugation at 13,200 rpm for 10 minutes. The supernatant was removed and labeled as 'cell lysate'.

Each strain was amplified using Tsp oligos pair.

The DNA was amplified using a standard PCR procedure.

| | |
|---|---|
| 5 ul | Buffer x10 (Roche) |
| 1 ul | dNTP mix (Roche, 10 mM mix) |
| 1.5 ul | 5' oligo (5 pmol) |
| 1.5 ul | 3' oligo (5 pmol) |
| 2 ul | Cell lysate |
| 0.5 ul | Taq DNA polymerase (Roche 5 U/ul) |
| 38.5 ul | H2O |
| PCR cycle. | |
| 94° C. | 1 minute |
| 94° C. | 1 minute) |
| 55° C. | 1 minute) repeated for 30 cycles |
| 72° C. | 1 minute) |
| 72° C. | 10 minutes |

Once the reactions were complete 25 ul was removed to a new microfuge tube for digestion with Ase I. To the 25 ul of PCR reaction 19 ul of H$_2$O, 5 ul of buffer 3 (NEB), 1 ul of Ase I (NEB) was added, mixed and incubated at 37° C. for 2 hours.

To the remaining PCR reaction 5 ul of loading buffer (×6) was added and 20 ul was loaded onto a 0.8% TAE 200 ml agarose gel (Invitrogen) plus Ethidium Bromide (5 ul of 10 mg/ml stock) and run at 100 volts for 1 hour. 10 ul of size marker (Perfect DNA marker 0.1-12 Kb, Novagen) was loaded in the final lane.

Once the Ase I digestions were complete 10 μl of loading buffer (×6) was added and 20 ul was loaded onto a 0.8% TAE agarose gel (Invitrogen) plus Ethidium Bromide (5 ul of 10 mg/ml stock) and run at 100 volts for 1 hour. 10 ul of size marker (Perfect DNA marker 0.1-12 Kb, Novagen) was loaded in the final lane. Both gels were visualized using UV transluminator.

The genomic fragment amplified showed the correct sized band of 2.8 Kb for Tsp. Following digestion with Ase I this confirmed the presence of the introduced Ase I sites in the Tsp deficient strain MXE001 but not in the W3110 control.

MXE001: genomic DNA amplified using the Tsp primer set and the resulting DNA was digested with Ase I to produce 2.2 and 0.6 Kbps bands.

W3110 PCR amplified DNA was not digested by Ase I restriction enzyme.

Generation of Cell Lines Carrying Mutated Spr Gene and Cell Lines Carrying Mutated Tsp Gene and Mutated Spr Gene The spr mutations were generated and selected for using a complementation assay.

The spr gene was mutated using the Clontech® random mutagenesis diversity PCR kit which introduced 1 to 2 mutations per 1000 bp. The mutated spr PCR DNA was cloned into an inducible expression vector [pTTO CDP870] which expresses CDP870 Fab' along with the spr mutant. This ligation was then electro-transformed into an *E. coli* strain MXE001 (ΔTsp) prepared using the method found in Miller, E. M. and Nickoloff, J. A., "*Escherichia coli* electrotransformation," in Methods in Molecular Biology, vol. 47, Nickoloff, J. A. (ed.), Humana Press, Totowa, N.J., 105 (1995). The following protocol was used: 40 ul of electro competent MXE001, 2.5 ul of the ligation (100 pg of DNA) was added to a 0.2 cm electroporation cuvette, electro-transformation was performed using a BioRad Genepulser Xcell with the following conditions, 2500V, 25 μF and 200Ω. After the electro-transformation 1 ml of SOC (Invitrogen) (pre-warmed to 37° C.) was added and the cells left to recover at 37° C. for 1 hour with gentle agitation.

The cells where plated onto Hypotonic agar (5 g/L Yeast extract, 2.5 g/L Tryptone, 15 g/L Agar (all Difco)) and incubated at 40° C. Cells which formed colonies were re-plated onto HLB at 43° C. to confirm restoration of the ability to grow under low osmotic conditions at high temperature to the MXE001 strain. Plasmid DNA was prepared from the selected clones and sequenced to identify spr mutations.

Using this method five single and one double mutation in the spr protein were isolated which complemented the ΔTsp phenotype as follows:
 1. V98E
 2. D133A
 3. V135D
 4. V135G
 5. G147C
 6. S95F and Y115F The individual mutations identified above and three catalytic triad mutations of spr (C94A, H145A, H157A) and W174R were used to generate new strains using either the wild-type W3110 *E. coli* strain (genotype: F-LAM-IN (rrnD-rrnE)1 rph1 (ATCC no. 27325)) to create spr mutated strains or MXE001 strain from Example 1 to make combined ΔTsp/mutant spr strains.

The following mutant *E. coli* cell strains were generated using a gene replacement vector system using the pKO3 homologous recombination/replacement plasmid (Link et al., 1997, *Journal of Bacteriology*, 179, 6228-6237), as described in Example 1 for the generation of MXE001.

TABLE 1

| Mutant *E. coli* Cell Strain | Genotype | Spr Vectors |
| --- | --- | --- |
| MXE001 | ΔTsp | — |
| MXE008 | ΔTsp, spr D133A | pMXE339, pK03 spr D133A (-SalI) |
| MXE009 | ΔTsp, spr H157A | pMXE345, pK03 spr H157A (-SalI) |
| MXE010 | spr G147C | pMXE338, pK03 spr G147C (-SalI) |
| MXE011 | spr C94A | pMXE343, pK03 spr C94A (-SalI) |
| MXE012 | spr H145A | pMXE344, pK03 spr H145A (-SalI) |
| MXE013 | spr W174R | pMXE346, pK03 spr W174R (-SalI) |
| MXE014 | ΔTsp, spr V135D | pMXE340, pK03 spr V135D (-SalI) |
| MXE015 | ΔTsp, spr V98E | pMXE342, pK03 spr V98E (-SalI) |
| MXE016 | ΔTsp, spr C94A | pMXE343, pK03 spr C94A (-SalI) |
| MXE017 | ΔTsp, spr H145A | pMXE344, pK03 spr H145A (-SalI) |
| MXE018 | ΔTsp, spr V135G | pMXE341, pK03 spr V135G (-SalI) |

The mutant spr integration cassettes were moved as Sal I, Not I restriction fragments into similarly restricted pKO3 plasmids.

The plasmid uses the temperature sensitive mutant of the pSC101 origin of replication (RepA) along with a chloramphenicol marker to force and select for chromosomal integration events. The sacB gene which encodes for levansucrase is lethal to *E. coli* grown on sucrose and hence (along with the chloramphenicol marker and pSC101 origin) is used to force and select for de-integration and plasmid curing events. This methodology had been described previously (Hamilton et al., 1989, *Journal of Bacteriology*, 171, 4617-4622 and Blomfield et al., 1991, *Molecular Microbiology*, 5, 1447-1457). The pKO3 system removes all selective markers from the host genome except for the inserted gene. The pK03 vectors listed below were constructed, comprising the mutated spr genes including a silent mutation within the spr sequence which removes a SalI restriction site for clone identification.

pMXE336, pK03 spr S95F (-SalI)
pMXE337, pK03 spr Y115F (-SalI)
pMXE338, pK03 spr G147C (-SalI)
pMXE339, pK03 spr D133A (-SalI)
pMXE340, pK03 spr V135D (-SalI)
pMXE341, pK03 spr V135G (-SalI)
pMXE342, pK03 spr V98E (-SalI)
pMXE343, pK03 spr C94A (-SalI)
pMXE344, pK03 spr H145A (-SalI)
pMXE345, pK03 spr H157A (-SalI)
pMXE346, pK03 spr W174R (-SalI)

These plasmids were then transformed into chemically competent *E. coli* W3110 cells prepared using the method found in Miller, E. M. and Nickoloff, J. A., "*Escherichia coli* electrotransformation," in Methods in Molecular Biology, vol. 47, Nickoloff, J. A. (ed.), Humana Press, Totowa, N.J., 105 (1995) or into MXE001 strain from Example 1 to make combined ΔTsp/mutant spr strains, as shown in Table 1.

Day 1 40 μl of electro-competent *E. coli* cells or MXE001 cells were mixed with (10 pg) 1 μl of pKO3 DNA in a chilled BioRad 0.2 cm electroporation cuvette before electroporation at 2500V, 25 μF and 200Ω. 1000 μl of 2×PY was added immediately, the cells recovered by shaking at 250 rpm in an incubator at 30° C. for 1 hour. Cells were serially 1/10 diluted in 2×PY before 100 μl aliquots were plated out onto 2×PY agar plates containing chloramphenicol at 20 μg/ml prewarmed at 30° C. and 43° C. Plates were incubated overnight at 30° C. and 43° C.

Day 2 The number of colonies grown at 30° C. gave an estimate of the efficiency of electroporation whilst colonies that survive growth at 43° C. represent potential integration events. Single colonies from the 43° C. plate were picked and resuspended in 10 ml of 2×PY. 100 μl of this was plated out onto 2×PY agar plates containing 5% (w/v) sucrose pre-warmed to 30° C. to generate single colonies. Plates were incubated overnight at 30° C.

Day 3 Colonies here represent potential simultaneous de-integration and plasmid curing events. If the de-integration and curing events happened early on in the growth, then the bulk of the colony mass will be clonal. Single colonies were picked and replica plated onto 2×PY agar that contained either chloramphenicol at 20 μg/ml or 5% (w/v) sucrose. Plates were incubated overnight at 30° C.

Day 4 Colonies that both grow on sucrose and die on chloramphenicol represent potential chromosomal replacement and plasmid curing events. These were picked and screened by PCR plus restriction digest for the loss of a SalI site. Colonies that generated a positive PCR band of the correct size and resistance to digestion by SalI were struck out to produce single colonies on 2×PY agar containing 5% (w/v) sucrose and the plates were incubated overnight at 30° C.

Day 5 Single colonies of PCR positive, chloramphenicol sensitive and sucrose resistant *E. coli* were used to make glycerol stocks, chemically competent cells and act as PCR templates for a PCR reaction with 5' and 3' flanking oligos to generate PCR product for direct DNA sequencing using Taq polymerase to confirm the correct mutation.

Generation of Plasmid for Fab' and DsbC Expression

A plasmid was constructed containing both the heavy and light chain sequences of an anti-TNF Fab' and the sequence encoding DsbC.

A dicistronic message was created of the anti-TNFα Fab' fragment (referred to as CDP870) described in WO01/94585. The upstream cistron encoded the light chain of the antibody (SEQ ID NO: 9) whilst the downstream cistron encoded the heavy chain of the antibody (SEQ ID NO: 10). A DNA sequence encoding the OmpA signal peptide was fused to the 5' end of the DNA coding for each of the light chain and the heavy chain to allow efficient secretion to the periplasm. The intergenic sequence (IGS) 2 was used as shown in SEQ ID NO: 16.

Plasmid pDPH358 (pTTO 40.4 CDP870 IGS2), an expression vector for the CDP870 Fab' (an anti-TNF Fab') and DsbC (a periplasmic polypeptide), was constructed using conventional restriction cloning methodologies which can be found in Sambrook et al 1989, Molecular cloning: a laboratory manual. CSHL press, N.Y. The plasmid pDPH358 contained the following features; a strong tac promoter and lac operator sequence. The plasmid contained a unique EcoRI restriction site after the coding region of the Fab' heavy chain, followed by a non-coding sequence and then a unique NdeI restriction site. The DsbC gene was PCR cloned using W3110 crude chromosomal DNA as a template such that the PCR product encoded for a 5' EcoRI site followed by a strong ribosome binding, followed by the native start codon, signal sequence and mature sequence of DsbC, terminating in a C-terminal His tag and finally a non-coding NdeI site. The EcoRI-NdeI PCR fragment was restricted and ligated into the expression vector such that all three polypeptides: Fab' light chain, Fab' heavy chain and DsbC were encoded on a single polycistronic mRNA.

The Fab light chain, heavy chain genes and DcbC gene were transcribed as a single polycistronic message. DNA encoding the signal peptide from the *E. coli* OmpA protein was fused to the 5' end of both light and heavy chain gene sequences, which directed the translocation of the polypeptides to the *E. coli* periplasm. Transcription was terminated using a dual transcription terminator rrnB tlt2. The lacIq gene encoded the constitutively expressed Lac I repressor protein. This repressed transcription from the tac promoter until de-repression was induced by the presence of allolactose or IPTG. The origin of replication used was p15A, which maintained a low copy number. The plasmid contained a tetracycline resistance gene for antibiotic selection.

Expression of Anti-TNF Fab' and DsbC

The MXE008 strain was transformed with the plasmid encoding Fab' light chain, Fab' heavy chain and DsbC.

The transformation of the strain was carried out using the method found in Chung C. T et al Transformation and storage of bacterial cells in the same solution. PNAS 86:2172-2175 (1989).

Expression of Anti-TNF Fab'

The strain MXE008 was transformed with plasmid pMXE117 (pTTO CDP870 or 40.4 IGS2), an expression vector for the CDP870 Fab' (an anti-TNF Fab' having a light chain sequence shown in SEQ ID NO: 9 and a heavy chain sequence shown in SEQ ID NO: 10), which was constructed using conventional restriction cloning methodologies which can be found in Sambrook et al 1989, Molecular cloning: a laboratory manual. CSHL press, N.Y. The plasmid pMXE117 (pTTO CDP870 or 40.4 IGS2) contained the following features; a strong tac promoter and lac operator sequence. The Fab light and heavy chain genes were transcribed as a single dicistronic message. DNA encoding the signal peptide from the *E. coli* OmpA protein was fused to the 5' end of both light and heavy chain gene sequences, which directed the translocation of the polypeptides to the *E. coli* periplasm. Transcription was terminated using a dual transcription terminator rrnB tlt2. The lacIq gene encoded the constitutively expressed Lac I repressor protein. This repressed transcription from the tac promoter until de-repression was induced by the presence of allolactose or IPTG. The origin of replication used was p15A, which maintained a low copy number. The plasmid contained a tetracycline resistance gene for antibiotic selection.

The transformation of the strains was carried out using the method found in Chung C. T et al Transformation and storage of bacterial cells in the same solution. PNAS 86:2172-2175 (1989).

Example 2: Growth of Host Cell Expressing Recombinant Antibody anti-TNF Fab'

The MXE008 strain produced in Example 1 was used in fermentation experiments to express the anti-TNFα Fab'.

MXE008 expressing anti-TNF Fab' and DsbC was fermented using standard fermentation conditions and medium. Following fermentation the resulting host cell sample was subjected to centrifugation and the cell pellet was frozen for storage.

Example 3: Extraction of Anti-TNFα Fab' from *E. coli* Strain & pH Adjustment The frozen pellet cell pellet from Example 2 was then thawed and re-suspended in extraction buffer (0.1M Tris/10 mM EDTA pH 7.4). Extraction was carried out overnight at 60° C.

Following the extraction step the extraction sample was centrifuged for 1 hour at 4200 rpm at 4° C. Post centrifugation the sample was clarified via a 0.45 um+0.22 um filtration.

After filtration, the resulting host cell sample extract having a pH of 6.9 was divided into 3 aliquots of 10 mL and was adjusted to pH 5.0, 4.5 or 3.0 using 30% (v/v) glacial acetic acid. A separate aliquot was retained at pH 6.9 as a control sample.

As can be seen in FIG. 1, increased levels of precipitation were observed as the pH decreased. The most precipitation of host cell protein was seen at pH3.0, followed by pH 4:5 and then pH 5.0.

Example 4: Analysis of Host Cell Sample Extracts Following pH Adjustment by Reverse Phase HPLC Samples of each host cell sample extract following pH adjustment to pH 5.0, 4.5 or 3.0 or the control (no-pH adjustment, pH 7) were taken across the time course at time (T)=0, T=1 hour, T=2 hours, T=4.5 hours, T=8 hours and T=24 hours, and real time analysis was carried out via reverse phase HPLC. The reverse phase HPLC allows separation of proteins on the basis of hydrophobicity and was carried out using a suitable HPLC column (Poroshell™ 300SB-C8, 5 micron, 2.1×75 mm from Agilent Technologies). Samples were filtered (0.22 um) prior to analysis.

The results are shown in FIGS. 2, 3, 5 and 6. FIG. 2 shows the overlaid chromatograms for the reverse phase HPLC analysis at T=0 (T=0 means as soon as was possible to conduct the analysis after pH adjustment, typically around 7 minutes after pH adjustment) for the host cell sample extract after pH adjustment. FIG. 3 shows the individual chromatograms for the reverse phase HPLC analysis at T=0 for the host cell sample extract after pH adjustment. The peaks corresponding to the light chain (LC) of the Fab', the heavy chain (HC) of the Fab', the whole Fab', the DsbC-his (his-tagged DsbC) and dipeptide binding protein (DBP) are shown for pH 7 and for pH adjustment to pH 3.0, pH 4.5 and pH 5.0. It can be seen from FIGS. 2 and 3 that the quantity of DsbC-his is lower after pH adjustment to pH 5 compared to the control at pH 7, the quantity of DsbC-his is significantly lowered further after pH adjustment to pH 4.5 or to pH 3.0. It can also be seen that the quantity of DBP is significantly lowered after pH adjustment to pH 3. The pI of DBP is 5.7. Therefore, in the host cell extract the pH had to be significantly lowered in order cause precipitation of DBP. The quantity of Fab' is not significantly affected by the pH adjustment.

Figure 5:
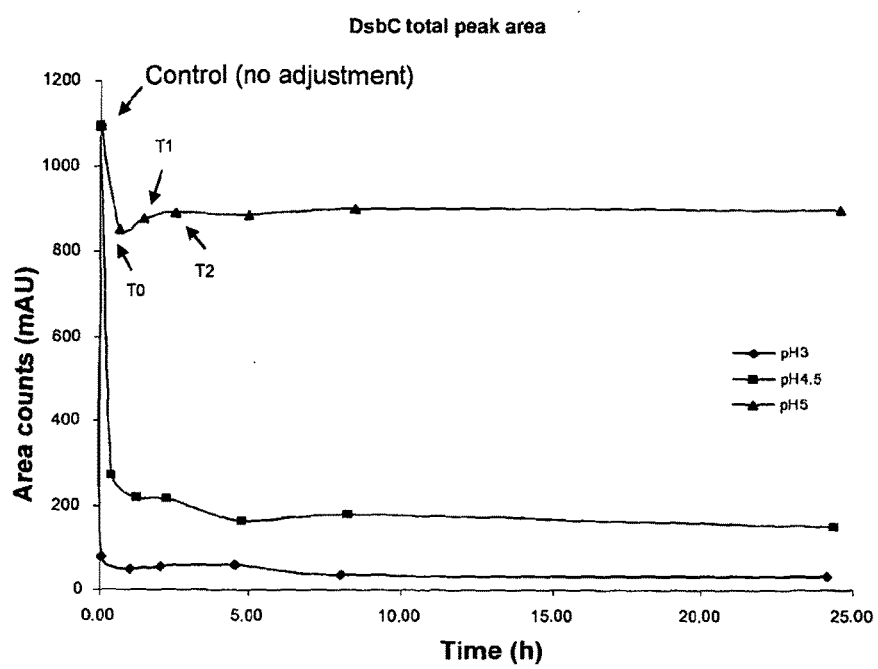
FIG. 5 shows the total peak area for DsbC from a reverse phase HPLC analysis at various time points for host cell solutions after pH adjustment to pH 5, pH 4.5 or pH 3 compared to the control pH of 7.

FIG. 5 shows the total peak area for DsbC-his from the reverse phase HPLC chromatogram after pH adjustment to pH 3.0, 4.5 and 5.0. As seen in FIGS. 2 and 3, the amount of DsbC is reduced after adjustment to pH 5.0 and further reduced after adjustment to pH 4.5 or 3.0.

Figure 6:
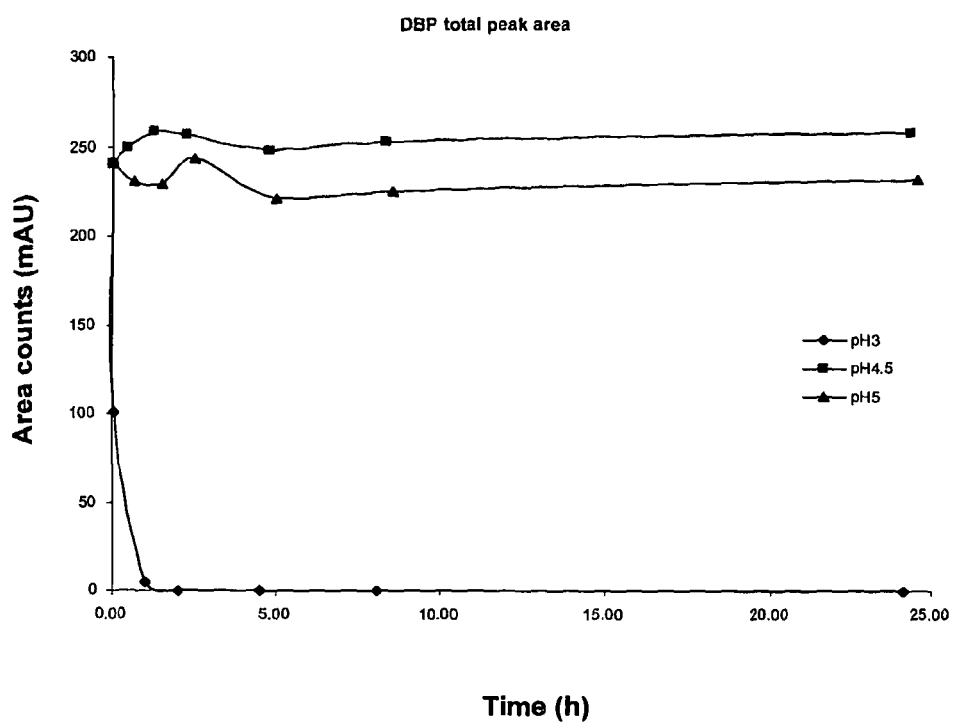
FIG. 6 shows the total peak area for DBP from a reverse phase HPLC analysis at various time points for host cell solutions after pH adjustment to pH 5, pH 4.5 or pH 3 compared to the control pH of 7.

FIG. 6 shows the total peak area for DBP from the reverse phase HPLC chromatogram after pH adjustment to pH 3.0, 4.5 and 5.0. As seen in FIGS. 2 and 3, the amount of DBP is reduced after adjustment to pH 3.0.

Figure 4:
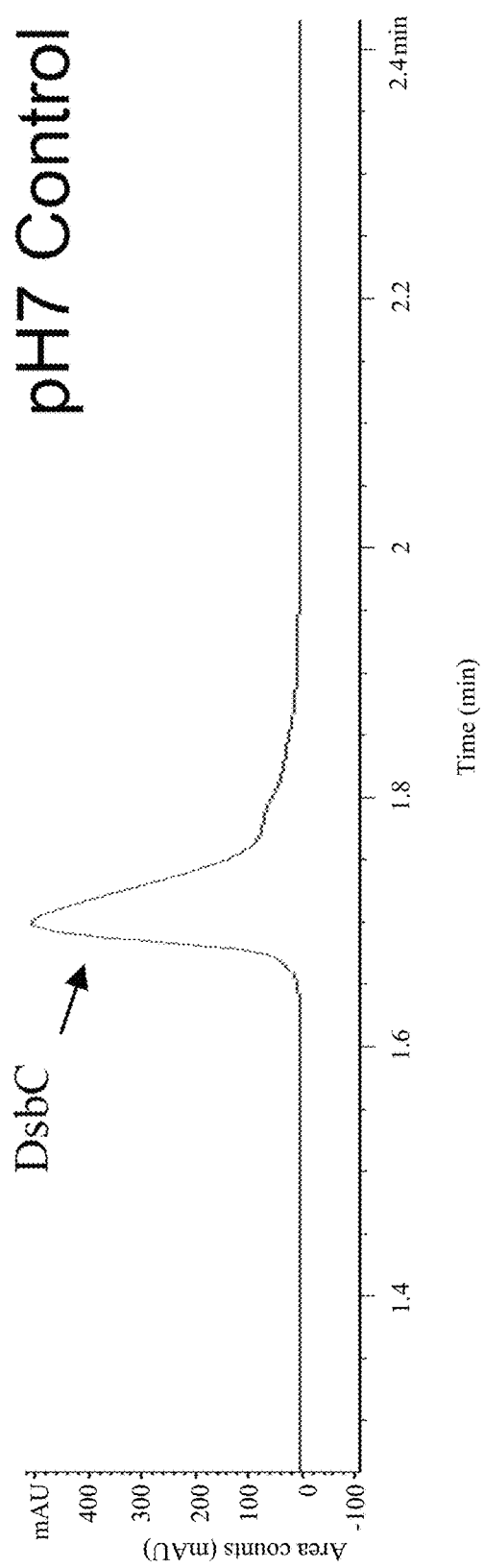
FIG. 4 shows the separate chromatograms of a reverse phase HPLC analysis for a solution comprising DsbC after pH adjustment to pH 3 after different time intervals compared to the control pH of 7.
Figure 4:
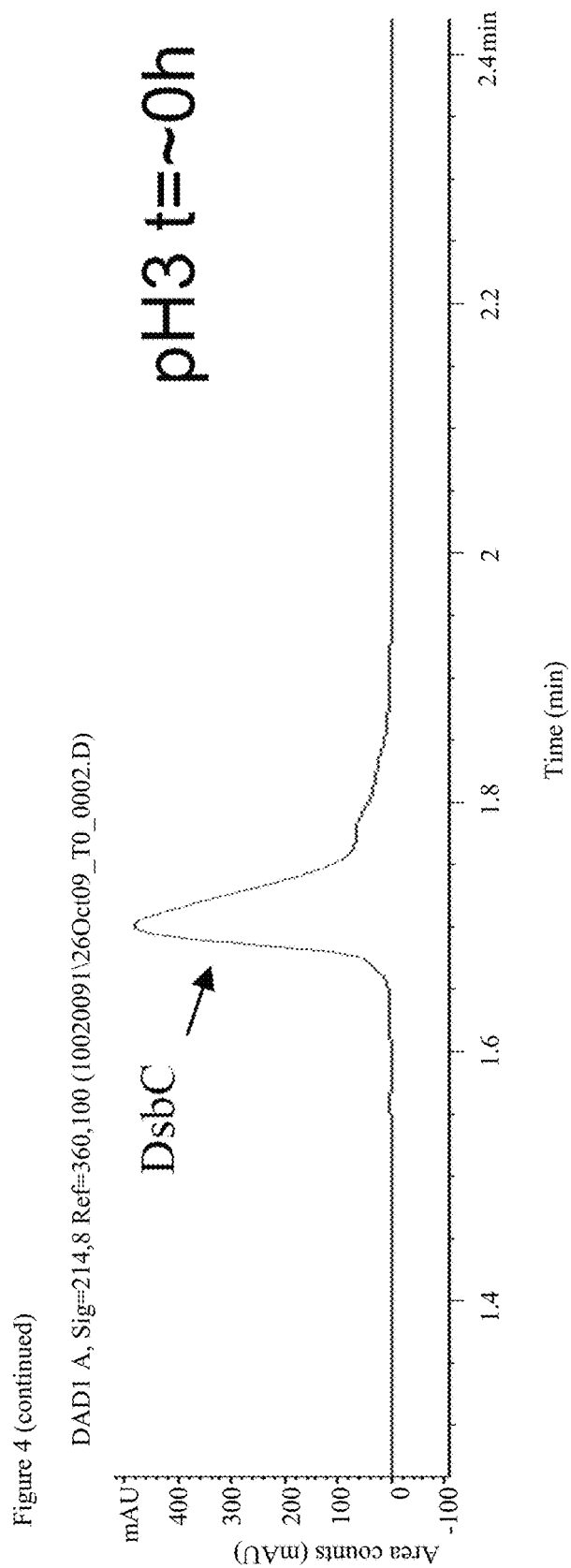
Figure 4:
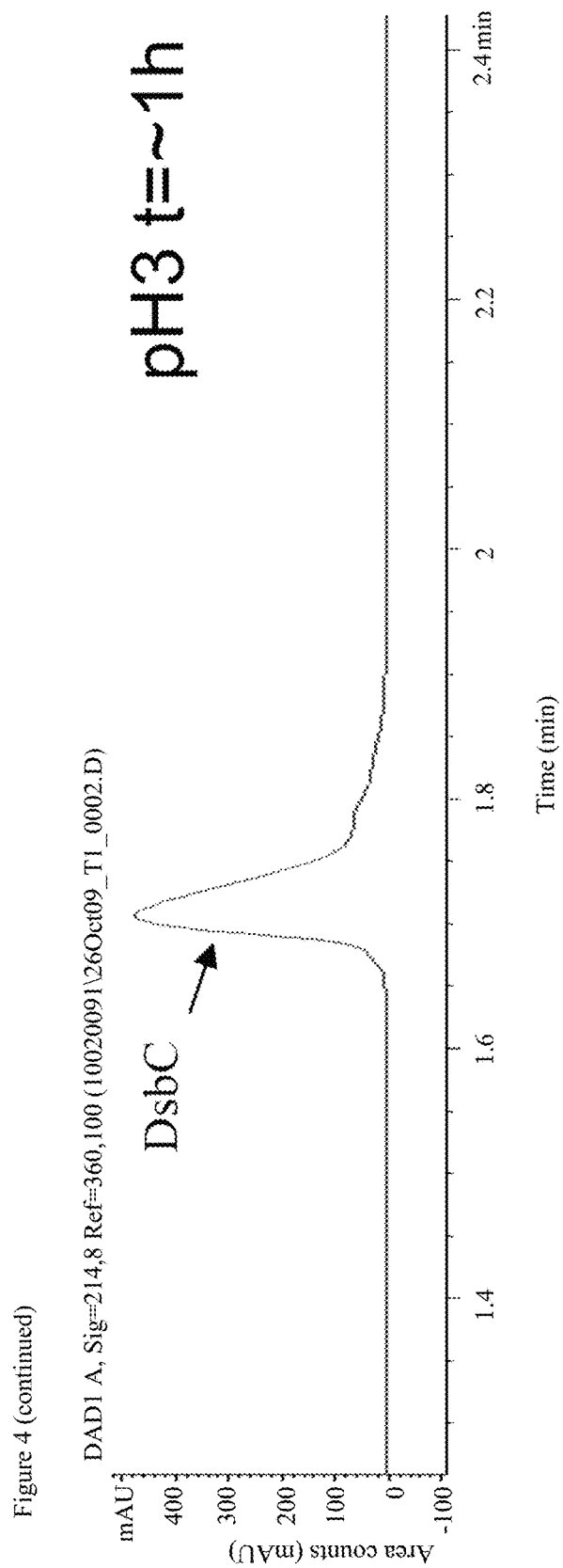
Figure 4:
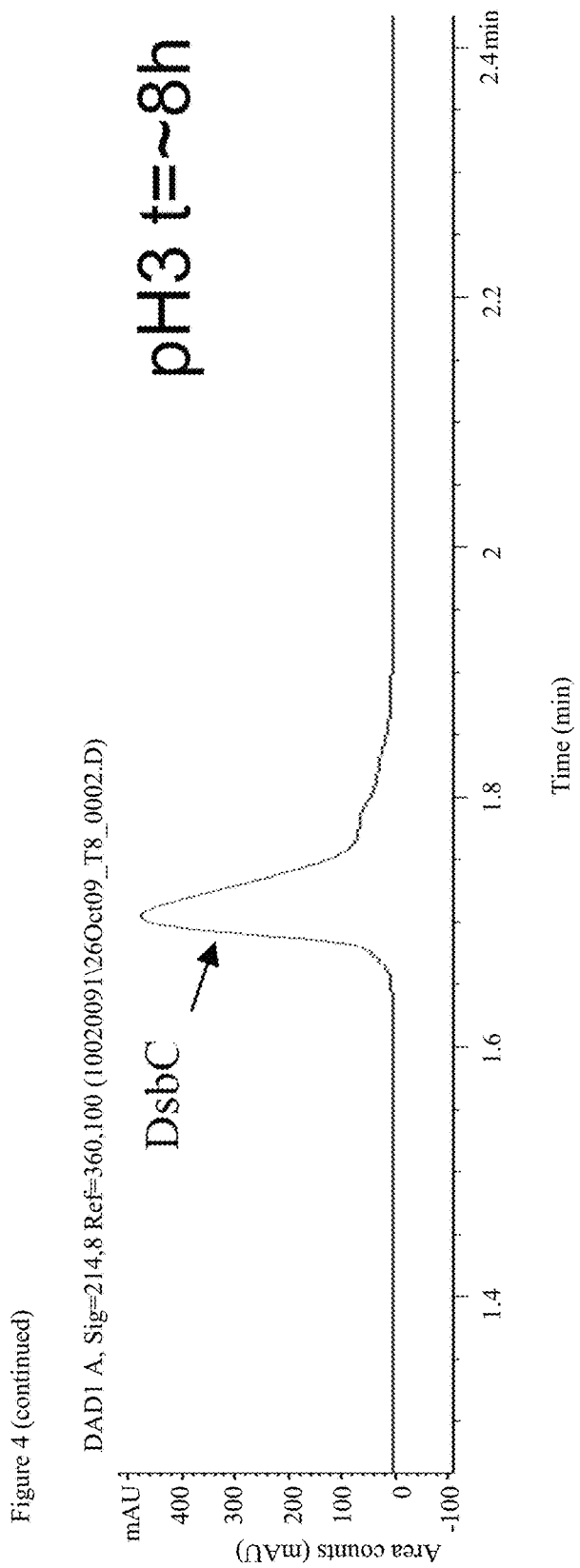
Figure 4:
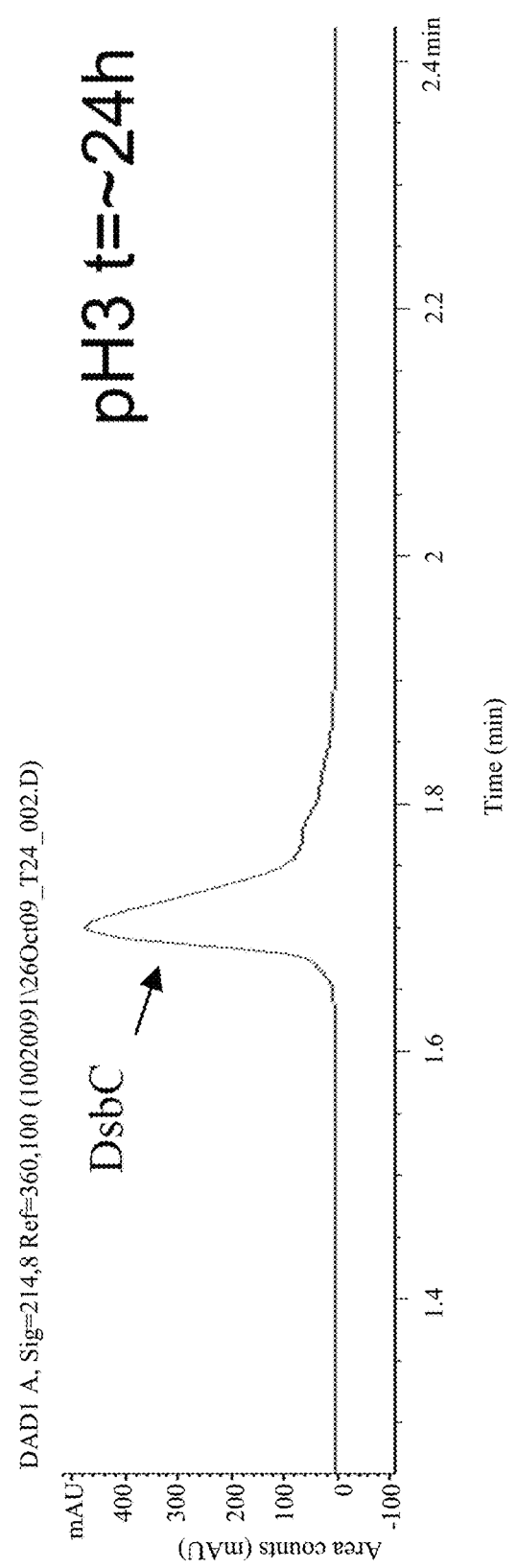

A purified solution of DsbC-his was obtained from the host cell extract of strain MXE008 by mixed-mode cation exchange chromatography. Analysis of this purified solution comprising DsbC-his was performed at pH 7 and at pH 3.0 after T=0, 1, 8 and 24 hours. The results are shown in FIG. 4 which shows the chromatograms for reverse phase HPLC analysis of the purified solution comprising DsbC-his at pH 7 and at pH 3.0 after T=0, 1, 8 and 24 hours. It can be seen from FIG. 4 that the pH adjustment had no effect on the precipitation and removal of DsbC-his from the solution.

Example 5: SDS-PAGE Analysis of Samples

Figure 7:
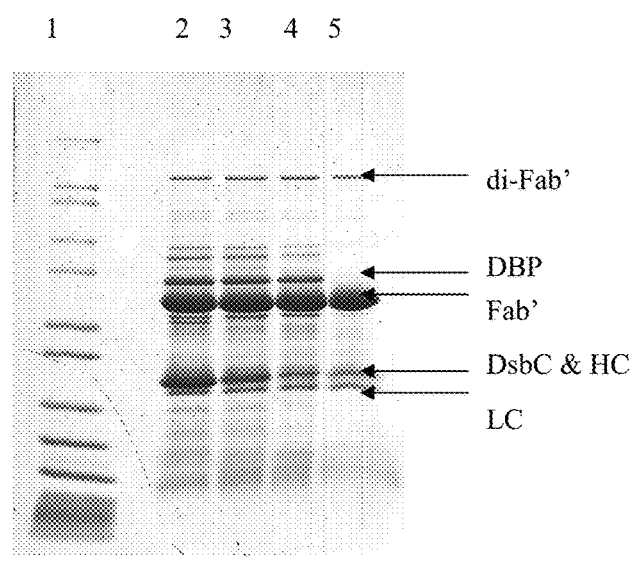
FIG. 7 shows the SDS-PAGE Analysis Gel for host cell solutions after pH adjustment to pH 5, pH 4.5 or pH 3 compared to the control pH of 6.9.

Non-reducing SDS-PAGE analysis was carried out after an extended storage at pH 7, pH 5.0, pH 4.5 and pH 3.0. FIG. 7 shows the SDS-PAGE analysis gel. It can be seen from FIG. 7 that the quantity of DBP is reduced after pH adjustment to pH 3. The DsbC and the heavy chain (HC) of the Fab' show at the same molecular weight on the gel, but it can be seen that the band for DsbC and HC is reduced following pH adjustment to pH 5, pH 4.5 and pH 3 due to the reduction in DsbC confirming that the quantity of DsbC-his and DBP is reduced after pH adjustment.

The anti-TNF Fab' CDP870 tested in the above examples after pH adjustment to pH 4.5 has been tested by Biacore analysis and found to have retained affinity to TNF. (data not shown).

The invention claimed is:

1. A method for purifying a recombinant protein of interest from gram-negative bacterial host cells, wherein said gram-negative bacterial host cells express the recombinant protein of interest and a recombinant disulphide isomerase, wherein the method comprises:
collecting said gram-negative bacterial host cells from culture medium;
releasing said recombinant protein of interest and said recombinant disulphide isomerase from said collected gram-negative bacterial host cells to form a gram-negative bacterial host cell extract;
separating said gram-negative bacterial host cells from the released recombinant protein of interest in said gram-negative bacterial host cell extract to form a liquid gram-negative bacterial host cell extract, wherein the pH of the liquid gram-negative bacterial host cell extract is lower than the pI of the recombinant protein of interest;
adjusting the pH of the liquid gram-negative bacterial host cell extract to a pH of 5 or less to precipitate the recombinant disulphide isomerase from the recombinant protein of interest, which remains in solution; and
separating the precipitated recombinant disulphide isomerase from the recombinant protein of interest remaining in solution to produce a liquid recombinant protein sample containing a reduced quantity of recombinant disulphide isomerase compared to the quantity of recombinant disulphide isomerase prior to said separating step.

2. The method according to claim 1, wherein the pH of the liquid gram-negative bacterial host cell extract is adjusted to a pH of 4.5 or less.

3. The method according to claim 2, wherein the pH of the liquid gram-negative bacterial host cell extract is adjusted to a pH of 4.5 to 3.0.

4. The method according to claim 2, wherein the pH of the liquid gram-negative bacterial host cell extract is adjusted to a pH of 3 or less.

5. The method according to claim 1, wherein the step of separating the precipitated recombinant disulphide isomerase from the recombinant protein of interest remaining in solution comprises centrifuging said liquid gram-negative bacterial host cell extract to separate the precipitate from the recombinant protein of interest to form said liquid recombinant protein sample and purifying said liquid recombinant protein of interest from said recombinant protein sample by chromatography.

6. The method according to claim 1, wherein the disulphide isomerase comprises a histidine tag.

7. The method according to claim 1, wherein the gram-negative bacterial host cells are *Escherichia coli* cells.

8. The method according to claim 1, wherein the gram-negative bacterial host cells comprise FKBP-type peptidyl-prolyl cis-trans isomerase (Fkpa) and/or seventeen kilodalton protein (Skp).

9. The method according to claim 1, wherein the pH of the liquid gram-negative bacterial host cell extract is adjusted to less than 5 using glacial acetic acid.

10. The method according to claim 1, wherein the liquid gram-negative bacterial host cell extract is held at a pH of 5 or less for one hour or less.

11. The method according to claim 1, wherein separating the precipitated recombinant disulphide isomerase from the recombinant protein of interest comprises centrifugation and/or filtration.

12. The method according to claim 1, said method further comprising a purification step of subjecting the liquid recombinant protein sample to chromatography.

13. The method according to claim 12, wherein the chromatography is ion-exchange chromatography.

14. The method according to claim 1, wherein the pH of the liquid recombinant protein sample is adjusted to a pH of 5 to 7.

15. The method according to claim 1, wherein releasing said recombinant protein of interest and said recombinant disulphide isomerase from said gram-negative bacterial host cells to form a gram-negative bacterial host cell extract comprises adding an extraction buffer to the gram-negative bacterial host cell extract and heating the gram-negative bacterial host cell extract/extraction buffer composition.

16. The method according to claim 1, wherein the recombinant protein of interest has a pI of 6 to 9.

17. The method according to claim 16, wherein the recombinant protein of interest has a pI of 8 to 9.

18. The method according to claim 1, wherein the recombinant protein of interest is a recombinant antibody.

19. The method according to claim 18, wherein the recombinant antibody is a monoclonal, humanized or chimeric antibody, or a binding fragment thereof.

20. The method according to claim 19, wherein the binding fragment is a Fab or Fab' fragment.

21. The method according to claim 18, wherein the recombinant antibody is specific for human TNFα.

22. The method according to claim 21, wherein the antibody comprises a heavy chain wherein the variable domain comprises a CDR having the sequence given in SEQ ID NO: 1 for CDRH1, SEQ ID NO: 2 for CDRH2, and SEQ ID NO: 3 for CDRH3 and a light chain and wherein the variable domain comprises a CDR having the sequence given in SEQ ID NO: 4 for CDRL1, SEQ ID NO: 5 for CDRL2 and SEQ ID NO: 6 for CDRL3.

23. The method according to claim 22, wherein the antibody comprises the light chain variable region sequence given in SEQ ID NO: 7 and the heavy chain variable region sequence given in SEQ ID NO: 8.

24. The method according to claim 23, wherein the antibody is a Fab fragment and comprises a heavy chain having the sequence given in SEQ ID NO: 10 and a light chain having the sequence given in SEQ ID NO: 9.

25. The method of claim 1, wherein the recombinant disulphide isomerase is disulphide isomerase A (DsbA), disulphide isomerase B (DsbB), disulphide isomerase C (DsbC), disulphide isomerase D (DsbD) or disulphide isomerase G (DsbG).

26. The method of claim 25, wherein the recombinant disulphide isomerase is disulphide isomerase C (DsbC).

27. The method according to claim 5, wherein the chromatography is ion-exchange chromatography.

28. The method according to claim 15, wherein said releasing said recombinant protein of interest and said recombinant disulphide isomerase from said gram negative bacterial host cells to form a gram-negative bacterial host cell extract comprises:

adding the extraction buffer to said gram-negative bacterial host cells separated from the culture medium to form the gram-negative bacterial host cell extract;

heating the gram-negative bacterial host cell extract to which said extraction buffer has been added to a temperature of 50° C. to 60° C. for a period of 10 to 16 hours;

centrifuging said heat treated gram-negative bacterial host cell extract/extraction buffer to separate gram-negative bacterial host cells from extracted material in the supernatant and collecting said supernatant;

adjusting the pH of said supernatant to between 3 and 5 to precipitate disulphide isomerase in said supernatant;

centrifuging the pH adjusted supernatant to separate precipitated disulphide isomerase from soluble proteins in said supernatant to form a recombinant protein sample;

optionally adjusting the pH of said recombinant protein sample to a pH of 5 to 7; and purifying said recombinant protein of interest from said recombinant protein sample by column chromatography.

29. The method according to claim 15, wherein releasing said recombinant protein of interest and said recombinant disulphide isomerase from said gram-negative bacterial host cells to form a gram-negative bacterial host cell extract comprises separating said gram-negative bacterial host cells from the culture medium, resuspending the separated gram-negative bacterial host cells in an extraction buffer and heating the gram-negative bacterial host cell/extraction buffer composition to a temperature between 30° C. and 70° C.

30. The method according to claim 29, wherein said gram-negative bacterial host cell/extraction buffer composition is heated to a temperature between 40° C. and 65° C.

31. The method according to claim 29, wherein said gram-negative bacterial host cell/extraction buffer composition is heated to a temperature between 40° C. and 60° C.

32. The method according to claim 29, wherein said gram-negative bacterial host cell/extraction buffer composition is heated to a temperature between 50° C. and 60° C.

33. The method according to claim 29, wherein said gram-negative bacterial host cell/extraction buffer composition is heated to a temperature between 30° C. and 70° C. for a period of between one (1) and 24 hours.

34. The method according to claim 29, wherein said gram-negative bacterial host cell/extraction buffer composition is heated to a temperature between 30° C. and 70° C. for a period of between four (4) and 24 hours.

35. The method according to claim 29, wherein said gram-negative bacterial host cell/extraction buffer composition is heated to a temperature between 30° C. and 70° C. for a period of between four (4) and 18 hours.

36. The method according to claim 29, wherein said gram-negative bacterial host cell/extraction buffer composition is heated to a temperature between 30° C. and 70° C. for a period of between six (6) and 16 hours.

37. The method according to claim 1, said method comprising adjusting the pH of the liquid gram-negative bacterial host cell extract to a pH of 3 to 5.

38. The method according to claim 37, wherein the pH of the liquid gram-negative bacterial host cell extract is held at a pH of 3 to 5 for a period of less than one hour and the pH is then raised to a pH of 5 to 7.

39. The method according to claim 1, wherein the step of collecting said gram-negative bacterial host cells from the culture medium comprises centrifugation of said gram-negative bacterial host cells to form a cell pellet and removal of the supernatant from said cell pellet.

40. The method according to claim 1, wherein the step of collecting said gram-negative bacterial host cells from the culture medium comprises filtering the cell culture containing said gram-negative bacterial host cells to separate said gram-negative bacterial host cells from said culture medium and recovering the filtered cell mass.

41. The method according to claim 1, wherein the step of collecting said gram-negative bacterial host cells from the culture medium comprises concentrating said gram-negative bacterial host cells in said culture medium and recovering the concentrated cell mass.

* * * * *